United States Patent [19]

Theodore et al.

[11] Patent Number: 5,578,287
[45] Date of Patent: Nov. 26, 1996

[54] THREE-STEP PRETARGETING METHODS USING IMPROVED BIOTIN-ACTIVE AGENT

[75] Inventors: Louis J. Theodore, Lynnwood; John M. Reno, Brier; Linda M. Gustavson, Seattle, all of Wash.

[73] Assignee: Neorx Corporation, Seattle, Wash.

[21] Appl. No.: 156,614

[22] Filed: Nov. 23, 1993

Related U.S. Application Data

[63] Continuation-in-part of PCT/US93/05406, Jun. 7, 1993, continuation-in-part of Ser. No. 995,383, Dec. 23, 1992, abandoned, which is a continuation-in-part of Ser. No. 895,588, Jun. 9, 1992, Pat. No. 5,283,342.

[51] Int. Cl.$^6$ .................... A61K 51/10; A61K 31/415; C07K 16/30; C07D 257/02

[52] U.S. Cl. .................... 424/1.49; 424/9.363; 424/1.53; 548/303.7; 514/387; 540/474; 530/391.5; 530/391.3; 530/391.1

[58] Field of Search ........................ 424/1.1, 85.8, 424/1.49, 1.53, 9.363; 530/391.1, 391.5, 391.3; 548/304; 514/387; 540/474

[56] References Cited

U.S. PATENT DOCUMENTS

| | | |
|---|---|---|
| 4,639,365 | 1/1987 | Sherry . |
| 4,647,447 | 3/1987 | Gries et al. . |
| 4,678,667 | 7/1987 | Meares et al. . |
| 4,863,713 | 9/1989 | Goodwin et al. . |
| 4,923,985 | 5/1990 | Gansow et al. . |
| 5,141,966 | 8/1992 | Porath . |
| 5,246,692 | 9/1993 | Gansow et al. . |
| 5,256,395 | 10/1993 | Barbet et al. . |
| 5,326,778 | 7/1994 | Rosebrough ............... 514/387 |

FOREIGN PATENT DOCUMENTS

| | | |
|---|---|---|
| 0327365 | 9/1989 | European Pat. Off. . |
| 0451824 | 10/1991 | European Pat. Off. . |
| 0496074 | 7/1992 | European Pat. Off. . |
| PCT/GB89/00427 | 7/1988 | WIPO . |
| PCT/EP90/00565 | 10/1990 | WIPO . |

OTHER PUBLICATIONS

Rosebrough, May 13, 1992, J. Nuclear Medicine, 33(5):880, Abstract 235.
Wolf et al., Meth. Enzym., 1990, 184:103.
Harris et al., 1993, Tibtech, 11:42.
Osband et al., Immunol. Today, 1990, 11:193.
Dermer, 1994, Biotechnology, 12:320.
Bloom, 1993, J. Clin. Invest., 91:1265.
Moore, 1991, Cancer, 67:2718.
Chatterjee, Cancer Immunol. Immunopathol., 1994, 38:75–82.
Curti, Crit. Rev. Oncol. Hematol., 1993, 14:29–39.
Jain, Scientific American, 1994, 271(1):58–65.
Zwierzina, Stem Cells, 1993, 11:144–153.
S. F. Rosebrough, "Plasma Stability and Pharmacokinetics of Radiolabeled Deferoxamine–Biotin Derivatives", J. Pharmacol. Exp. Ther., vol. 265, No. 1, Apr. 1993, pp. 408–415.
J. A. Sanderson et al, "Preparation and Characterization of Biotin Conjugates of Antipan–Carcinoma NR–LU–10 Monoclonal Antibody for a Three Step Radioimmunotherapy", J. Nucl. Med., vol. 33, 5th Suppl., Abstract 222, p. 880, May 13, 1992.
Sheldon et al., Appl. Radiat. Isot., vol. 43, No. 11, pp. 1399–1402, 1992, "Targeting of [$^{111}$n]Biocytin to Cultured Ovarian Adenocarcinoma Cells Using Covalent Monoclonal Antibody–Streptavidin Conjugates."
Goodwin, J. Nucl. Med., vol. 33, No. 10, pp. 1816–1818, 1992, "New Methods for Localizing Infection: A role for Avidin–Biotin?".
Goodwin, et al., J. Nucl. Med., vol. 33, No. 11, pp. 2006–2013, 1992, "Pretargeted Immunoscintigraphy: Effect of Hapten Valency on Murine Tumor Uptake."
McMurry et al., Bioconjugate Chem., vol. 3, No. 2, pp. 108–117, 1992, "Convenient Synthesis of Bifunctional Tetraaza Macrocycles."
Renn and Meares, Bioconjugate Chem., vol. 3, No. 6, pp. 563–569, 1992, "Large–Scale Synthesis of the Bifunctional Chelating Agent 2–(p–Nitrobenzyl)–1,4,7,10–tetraazacyclododecane–N,N',N'',N'''–tetraacetic Acid, and the Determination of Its Enatiomeric Purity by Chiral Chromatography.".
Koch and Macke, Angew. Chem. Intl. Ed. Engl., vol. 31, No. 11, pp. 1507–1509, 1992, "$^{99m}$Tc Labeled Biotin Conjugate in a Tumor Pretargeting Approach with Monoclonal antibodies."
Wu et al., Nucl. Med. Biol. Int. J. Radiat. Appl. Instrum. Part B, vol. 19, No. 2, pp. 239–244, 1992, "Investigations of N–Linked Macrocycles for $^{111}$In and $^{90}$Y Labeling of Proteins."
Goodwin et al., J. Nucl. Med., p. 880, 1992, Abstract No. 232, "Pharmacokinetics of Biotin–Chelate Conjugates for Pretargeted Avidin–Biotin Immunoscintigraphy."
Dischino et al., Inorg. Chem., vol. 30, pp. 1265–1269, 1992, "Synthesis of Nonionic Gadolinium Chelates Useful as Contrast Agents for Magnetic Resonance Imaging."
Sieving et al., Bioconjugate Chem., vol. 1, pp. 65–71, 1990, "Preparation and Characterization of Paramagnetic Polychelates and Their Protein Conjugates".
Parker et al., Pure & Appl. Chem., vol. 61, No. 9, pp. 1637–1641, 1989, "Implementation of macrocyclic conjugated antibodies for tumour–targeting."
Riesen et al., J. Chem. Soc., Chem. Commun., pp. 460–462, 1989, "Synthesis and X–Ray Structural Characterization of Seven Co–ordinate Macrocyclic In$^{3+}$ Complexes with Relevance to Radiopharmaceutical Applications."

(List continued on next page.)

Primary Examiner—Frank C. Eisenschenk
Attorney, Agent, or Firm—Burns, Doane, Swecker & Mathis, L.L.P.

[57] ABSTRACT

Methods, compounds, compositions and kits that relate to pretargeted delivery of diagnostic and therapeutic agents are disclosed. In particular, three-step pretargeting methods are described.

18 Claims, 2 Drawing Sheets

OTHER PUBLICATIONS

Moi and Meares, *J. Am. Chem. Soc.*, vol. 110, pp. 6267–6269, 1988, "The Peptide Way to Macrocyclic Bifunctional Chelating Agents: Synthesis of 2-(p-Nitrobenzyl)-1,4,7,10-tetraazacyclododecane-N,N',N",N"'-tetraacetic Acid and Study of Its Yttrium (III) Complex."

Kasprzyk and Wilkins, *Inorg. Chem.*, vol. 21, pp. 3349–3352, 1982, "Kinetics of Interaction of Metal Ions with Two Tetraaza Tetraacetate Macrocycles."

Green, *Biochem. J.*, 89:585, 1963, "The Use of [$^{14}$C]Biotin for Kinetic Studies and for Assay."

Kalofonos et al., *J. Nucl. Med.*, vol. 31, No. 11, pp. 1791–1796, 1990, "Imaging of Tumor in Patients with Indium-111-Labeled Biotin and Streptavidin-Conjugated Antibodies: Preliminary Communication."

Hnatowich et al., *J. Nucl. Med.*, vol. 28, No. 8, pp. 1294–1302, 1987, "Investigations of Avidin and Biotin for Imaging Applications.".

Paganelli et al., *Int. J. Cancer*, 45:1184–1189, 1990, "Intraperitoneal Radio-Localization of Tumors Pre-Targeted by Biotinylated Monoclonal Antibodies."

Paganelli et al., *Nuclear Medicine Communications*, 12:211–234, 1991, "Monoclonal antibody pretargeting techniques for tumour localization: the avidin-biotin system."

Goodwin/Hnatowich, *J. Nucl. Med.*, vol. 32, No. 4, pp. 750–751, 1991, Letter to the Editor/Reply.

Rosebrough, *J. Nucl. Med.*, p. 880, 1992, Abstract No. 235, "Plasma Stability and Pharmacokinetics of Radio-Labeled Deferoxamine-Biotin Derivatives."

Virzi et al., *J. Nucl. Med.*, p. 920, 1992, Abstract No. 403, "The Preparation and Evaluation of 12 Biotin Derivatives Labeled with Tc-99M."

Rosario et al., *J. Nucl. Med.*, vol. 32, No. 5, p. 993, 1991, Abstract No. 356, "Bolton-Hunter and Biotin Derivatized Polylysine: A New Multi-Valent Peptide Reagent for In Vivo Pre-Targeting with Streptavidin Conjugates."

THREE-STEP PRETARGETING METHODS USING IMPROVED BIOTIN-ACTIVE AGENT

CROSS REFERENCE TO RELATED APPLICATIONS

This application is a continuation-in-part of pending PCT Patent Application No. PCT/US93/05406, filed Jun. 7, 1993 and designating the United States, which, in turn, is a continuation-in-part of pending U.S. patent application Ser. No. 07/995,383, filed Dec. 23, 1992, now abandoned, which is, in turn, a continuation-in-part of pending U.S. patent application Ser. No. 07/895,588, filed Jun. 9, 1992, now U.S. Pat. No. 5,283,342.

TECHNICAL FIELD

The present invention relates to methods, compounds, compositions and kits useful for delivering to a target site a targeting moiety that is conjugated to one member of a ligand/anti-ligand pair. After localization and clearance of the targeting moiety conjugate, direct or indirect binding of a diagnostic or therapeutic agent conjugate at the target site occurs. Methods for radiometal labeling of biotin and for improved radiohalogenation of biotin, as well as the related compounds, are also disclosed.

SUMMARY OF THE INVENTION

The present invention describes three-step pretargeting diagnostic and therapeutic methods. Three-step pretargeting protocols feature administration of a targeting moiety-ligand conjugate, which is allowed to localize at a target site and to dilute in the circulation. Subsequently administered anti-ligand binds to the targeting moiety-ligand conjugate in both blood and at a target site and clears unbound antibody-ligand conjugate from the blood. A diagnostic or therapeutic agent-ligand conjugate that exhibits rapid whole body clearance is then administered and binds to the targeting moiety-ligand-anti-ligand localized at a target site, thereby constituting the third target site-localized component in the protocol.

Preferred three-step pretargeting methods of the present invention employ biotin/avidin as the ligand/anti-ligand binding pair. These preferred three-step pretargeting methods involve the administration of biotin conjugated to therapeutic or diagnostic radionuclides or other active agents such as chemotherapeutic drugs, anti-tumor agents such as cytokines and the like. Y-90-DOTA-biotin conjugates are particularly preferred in the practice of the present invention.

DETAILED DESCRIPTION OF THE INVENTION

Figure 1:
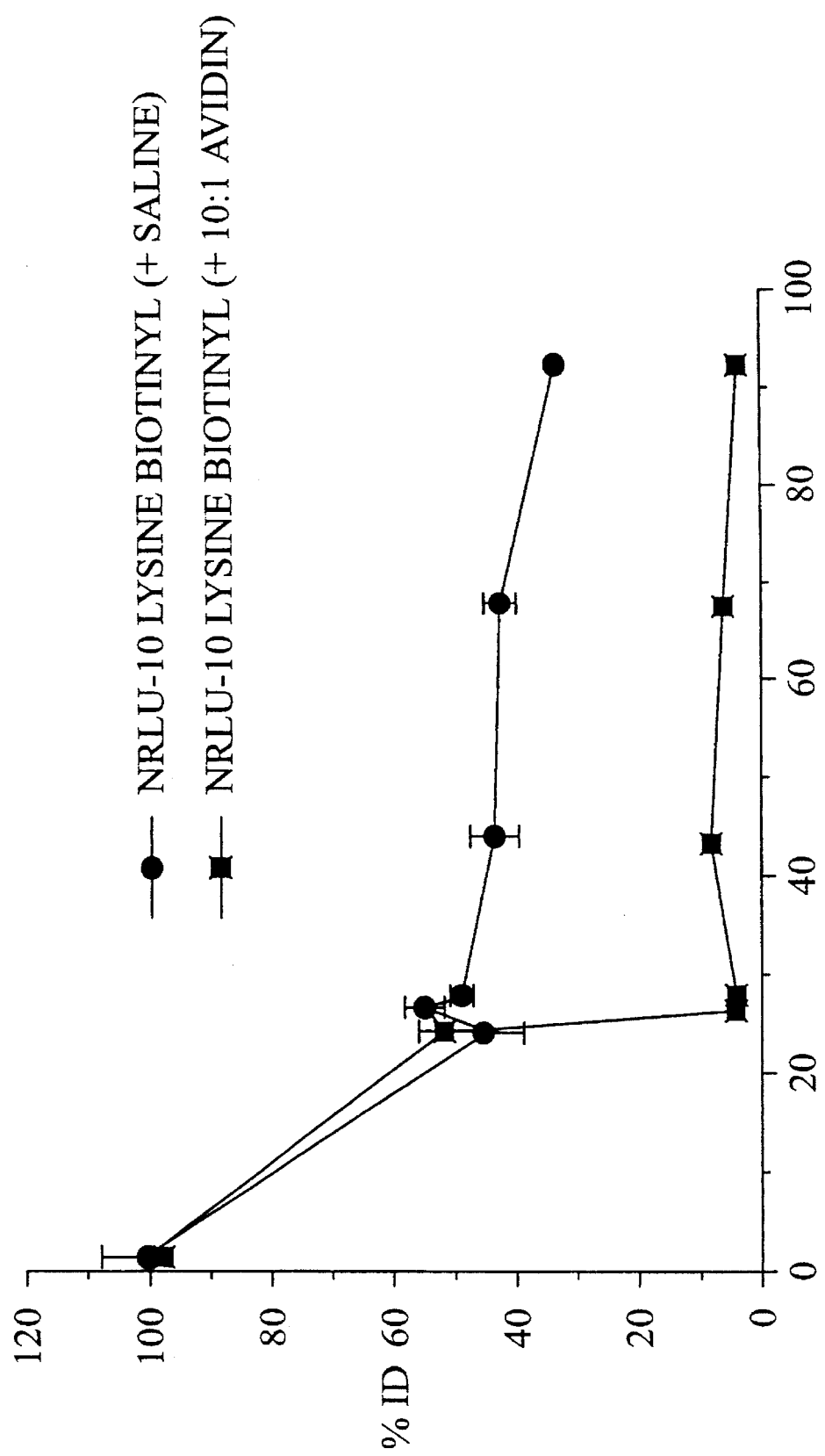
FIG. 1 illustrates blood clearance of biotinylated antibody following intravenous administration of avidin.

Prior to setting forth the invention, it may be helpful to set forth definitions of certain terms to be used within the disclosure.

Targeting Moiety

A molecule that binds to a defined population of cells. The targeting moiety may bind a receptor, an enzymatic substrate, an antigenic determinant, or other binding site present on the target cell population. Antibody is used throughout the specification as a prototypical example of a targeting moiety.

Ligand/Anti-Ligand Pair

A complementary/anti-complementary set of molecules that demonstrate specific binding, generally of relatively high affinity. Exemplary ligand/anti-ligand pairs include zinc finger protein/dsDNA fragment, enzyme/inhibitor, hapten/antibody, ligand/receptor, and biotin/avidin. Biotin/avidin is used throughout the specification as a prototypical example of a ligand/anti-ligand pair.

Anti-Ligand

As defined herein, an "anti-ligand" demonstrates high affinity, and preferably, multivalent binding of the complementary ligand. Preferably, the anti-ligand is large enough to avoid rapid renal clearance, and contains sufficient multivalency to accomplish crosslinking and aggregation of targeting moiety-ligand conjugates. Univalent anti-ligands also find utility in the practice of the present invention.

Avidin

As defined herein, "avidin" includes avidin, streptavidin and derivatives and analogs thereof that are capable of high affinity, multivalent or univalent binding of biotin.

Ligand

As defined herein, a "ligand" is a relatively small, soluble molecule that exhibits rapid serum, blood and/or whole body clearance when administered intravenously in an animal or human.

Active Agent

A diagnostic or therapeutic agent ("the payload"), including radionuclides, drugs, anti-tumor agents, toxins and the like.

$N_xS_y$ Chelates

As defined herein, the term "$N_xS_y$ chelates" includes bifunctional chelators that are capable of (i) coordinately binding a metal or radiometal and (ii) covalently attaching to a targeting moiety. Particularly preferred $N_xS_y$ chelates have $N_2S_2$ and $N_3S$ cores. Exemplary $N_xS_y$ chelates are described in Fritzberg et al., *Proc. Natl. Acad. Sci. U.S.A.* 85:4024–29, 1988; in Weber et al., *Bioconj. Chem.* 1:431–37, 1990; and in the references cited therein, for instance.

Pretargeting

As defined herein, pretargeting involves target site localization of a targeting moiety that is conjugated with one member of a ligand/anti-ligand pair; after a time period sufficient for optimal target-to-non-target accumulation of this targeting moiety conjugate, active agent conjugated to the opposite member of the ligand/anti-ligand pair is administered and is bound (directly or indirectly) to the targeting moiety conjugate at the target site (two-step pretargeting). Three-step pretargeting protocols are also provided by the present invention, involving, for example, administration of targeting moiety-ligand, administration of anti-ligand to clear circulating targeting moiety-ligand and to localize to previously target-localized targeting moiety ligand, and administration of active agent-ligand.

Conjugate

A conjugate encompasses chemical conjugates (covalently or non-covalently bound), fusion proteins and the like.

A recognized disadvantage associated with in vivo administration of targeting moiety-radioisotopic conjugates for imaging or therapy is localization of the attached radioactive agent at both non-target and target sites. Until the administered radiolabeled conjugate clears from the circulation, normal organs and tissues are transitorily exposed to the attached radioactive agent. For instance, radiolabeled whole antibodies that are administered in vivo exhibit relatively slow blood clearance; maximum target site localization generally occurs 1–3 days post-administration. Generally, the longer the clearance time of the conjugate from the circulation, the greater the radioexposure of non-target organs.

These characteristics are particularly problematic with human radioimmunotherapy. In human clinical trials, the long circulating half-life of radioisotope bound to whole antibody causes relatively large doses of radiation to be delivered to the whole body. In particular, the bone marrow, which is very radiosensitive, is the dose-limiting organ of non-specific toxicity.

In order to decrease radioisotope exposure of non-target tissue, potential targeting moieties generally have been screened to identify those that display minimal non-target reactivity, while retaining target specificity and reactivity. By reducing non-target exposure (and adverse non-target localization and/or toxicity), increased doses of a radiotherapeutic conjugate may be administered; moreover, decreased non-target accumulation of a radiodiagnostic conjugate leads to improved contrast between background and target.

Therapeutic drugs, administered alone or as targeted conjugates, are accompanied by similar disadvantages. Again, the goal is administration of the highest possible concentration of drug (to maximize exposure of target tissue), while remaining below the threshold of unacceptable normal organ toxicity (due to non-target tissue exposure). Unlike radioisotopes, however, therapeutic drugs need to be taken into a target cell to exert a cytotoxic effect. In the case of targeting moiety-therapeutic drug conjugates, it would be advantageous to combine the relative target specificity of a targeting moiety with a means for enhanced target cell internalization of the targeting moiety-drug conjugate.

In contrast, enhanced target cell internalization is disadvantageous if one administers diagnostic agent-targeting moiety conjugates. Internalization of diagnostic conjugates results in cellular catabolism and degradation of the conjugate. Upon degradation, small adducts of the diagnostic agent or the diagnostic agent per se may be released from the cell, thus eliminating the ability to detect the conjugate in a target-specific manner.

One method for reducing non-target tissue exposure to a diagnostic or therapeutic agent involves "pretargeting" the targeting moiety at a target site, and then subsequently administering a rapidly clearing diagnostic or therapeutic agent conjugate that is capable of binding to the "pretargeted" targeting moiety at the target site. A description of some embodiments of the pretargeting technique may be found in U.S. Pat. No. 4,863,713 (Goodwin et al.).

A typical pretargeting approach ("three-step") is schematically depicted below.

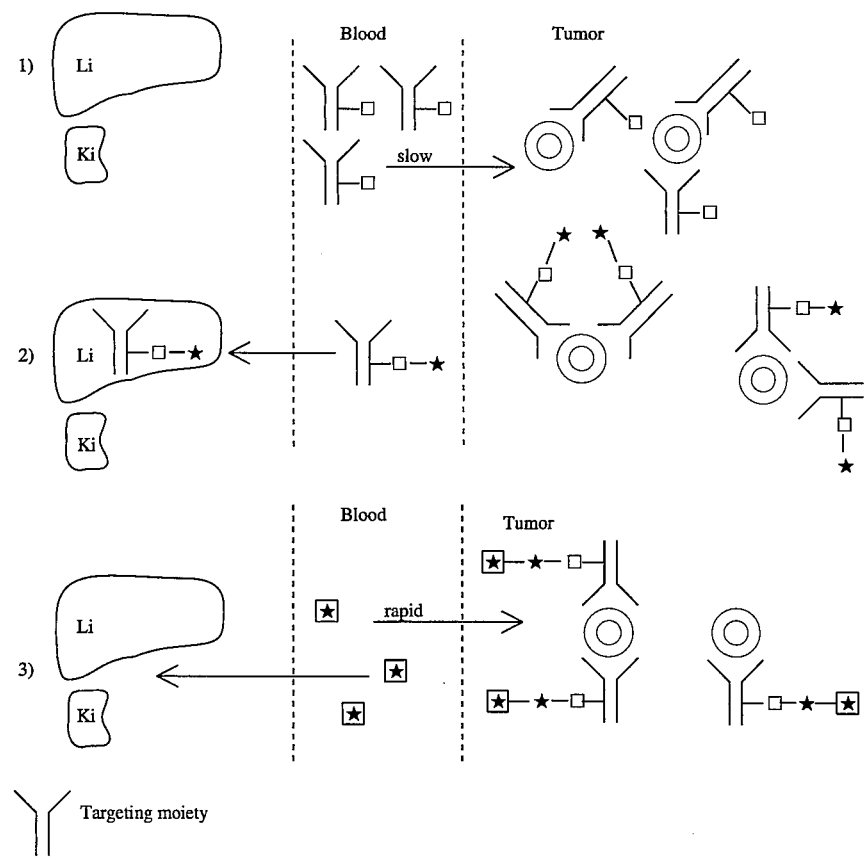

★ Anti-ligand
☐ Ligand
[★] Ligand-active agent

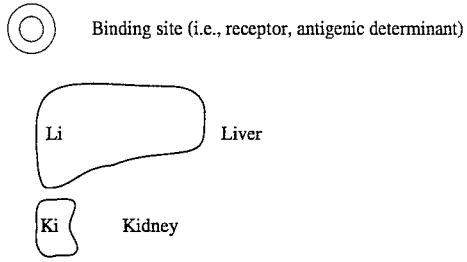

Binding site (i.e., receptor, antigenic determinant)

Li  Liver

Ki  Kidney

Briefly, this three-step pretargeting protocol features administration of an antibody-ligand conjugate, which is allowed to localize at a target site and to dilute in the circulation. Subsequently administered anti-ligand binds to the antibody-ligand conjugate and clears unbound antibody-ligand conjugate from the blood. Preferred anti-ligands are large and contain sufficient multivalency to accomplish crosslinking and aggregation of circulating antibody-ligand conjugates. The clearing by anti-ligand is probably attributable to anti-ligand crosslinking and/or aggregation of antibody-ligand conjugates that are circulating in the blood, which leads to complex/aggregate clearance by the recipient's RES. It is preferred that the ligand-anti-ligand pair displays relatively high affinity binding.

A diagnostic or therapeutic agent-ligand conjugate that exhibits rapid whole body clearance is then administered. When the circulation brings the active agent-ligand conjugate in proximity to the target cell-bound antibody-ligand-anti-ligand complex, anti-ligand binds the circulating active agent-ligand conjugate and produces an antibody-ligand:anti-ligand:ligand-active agent "sandwich" at the target site. Because the diagnostic or therapeutic agent is attached to a rapidly clearing ligand (rather than antibody, antibody fragment or other slowly clearing targeting moiety), this technique promises decreased non-target exposure to the active agent.

Alternate pretargeting methods eliminate the step of parenterally administering an anti-ligand clearing agent. These "two-step" procedures feature targeting moiety-ligand or targeting moiety-anti-ligand administration, followed by administration of active agent conjugated to the opposite member of the ligand-anti-ligand pair.

The present invention provides methods for radiolabeling biotin with technetium-99m, rhenium-186 and rhenium-188 are disclosed. Previously, biotin derivatives were radiolabeled with indium-111 for use in pretargeted immunoscintigraphy (for instance, Virzi et al., *Nucl. Med. Biol.* 18:719–26, 1991; Kalofonos et al., *J. Nucl. Med.* 31: 1791–96, 1990; Paganelli et al., *Canc. Res.,* 51:5960–66, 1991). However, $^{99m}$Tc is a particularly preferred radionuclide for immunoscintigraphy due to (i) low cost, (ii) convenient supply and (iii) favorable nuclear properties. Rhenium-186 displays chelating chemistry very similar to $^{99m}$Tc, and is considered to be an excellent therapeutic radionuclide (i.e., a 3.7 day half-life and 1.07 MeV maximum particle that is similar to $^{131}$I). Therefore, the claimed methods for technetium and rhenium radiolabeling of biotin numerous advantages.

The present invention is also directed to radiolabeling with yttrium-90, lutetium-177, sumarium-153, and other appropriate +3 metals. Y-90 is a particularly preferred beta particle emitting radionuclide for therapy, because it exhibits favorable nuclear properties including high specific activity, long path length with respect to deposition of radiation in tissue, high equilibrium dose constant and favorable half-life properties. More specifically, the beta emission of Y-90 ($Beta_{av}$=0.937 MeV) is one of the most energetic of all beta emitters. The $X_{90}$ value of Y-90 is 5.34 mm (i.e., 90% of the energy emitted from a point source is absorbed in a sphere of 5.34 mm radius). Y-90 has a high equilibrium dose constant or mean energy/nuclear transition, Delta=1.99 Rad-gram/microcurie-hour, and a 64 hour half-life suitable for targeted therapy. Y-90 can be manufactured at high specific activity and is available as a generator product. Specific advantages of Y-90 are (1) that it has the capability to kill neighboring target Cells not directly targeted by the pretargeted targeting moiety-ligand or targeting moiety-anti-ligand conjugate and (2) that more radiation is deposited per microcurie localized than for other beta emitters of lower mean particle energy (provided that a sufficiently large target volume is available).

Lu-177 is a particularly preferred radionuclide for targeted nuclide therapy, since it has a moderately energetic beta emission ($Beta_{av}$=0.140 MeV); it is available in high specific activity; its radiochemical production is efficient; it emits two gammas of ideal energy and abundance for imaging (208 keV, 11% and 113 keV, 7%); and it has a relatively long half-life (161 hours). The $X_{90}$ for Lu-177 is 0.31 mm, i.e., 90% of the energy emitted form a point source is absorbed in a sphere of radius 0.31 mm. Lu-177 has an equilibrium dose constant or mean energy/nuclear transition of 0.31 Rad-gram/microcuries-hour and an adequate half-life to serve as a targeted therapeutic radionuclide. Specific advantages of Lu-177 are (1) that its emitted energy is efficiently absorbed in smaller targeted tumor volumes such as metastatic tumor foci or involved lymph nodes and (2) that its long physical half-life makes optimal use of the tumor retention property of the pretargeting delivery method. Lu-177 has the additional advantage of being imagable by commonly available nuclear medicine cameras.

The "targeting moiety" of the present invention binds to a defined target cell population, such as tumor cells. Preferred targeting moieties useful in this regard include antibody and antibody fragments, peptides, and hormones. Proteins corresponding to known cell surface receptors (including low density lipoproteins, transferrin and insulin), fibrinolytic enzymes, anti-HER2, platelet binding proteins such as annexins, and biological response modifiers (including interleukin, interferon, erythropoietin and colony-stimulating factor) are also preferred targeting moieties. Also, anti-EGF receptor antibodies, which internalize following binding to the EGF receptor and which traffic to the nucleus, are preferred targeting moieties for use in the present invention to facilitate delivery of Auger emitters and nucleus binding drugs to target cell nuclei. Oligonucleotides, e.g., antisense oligonucleotides that are complementary to portions of target cell nucleic acids (DNA or RNA), are also useful as targeting moieties in the practice of the present invention. Oligonucleotides binding to cell surfaces are also useful. Analogs of the above-listed targeting moieties that retain the capacity to bind to a defined target cell population may also be used within the claimed invention. In addition, synthetic targeting moieties may be designed.

Functional equivalents of the aforementioned molecules are useful as targeting moieties of the present invention. One targeting moiety functional equivalent is a "mimetic" compound, an organic chemical construct designed to mimic the proper configuration and/or orientation for targeting moiety-target cell binding. Another targeting moiety functional equivalent is a short polypeptide designated as a "minimal" polypeptide, constructed using computer-assisted molecular modeling and mutants having altered binding affinity, which minimal polypeptides exhibit the binding affinity of the targeting moiety.

Preferred targeting moieties of the present invention are antibodies (polyclonal or monoclonal), peptides, oligonucleotides or the like. Polyclonal antibodies useful in the practice of the present invention are polyclonal (Vial and Callahan, *Univ. Mich. Med. Bull.,* 20: 284–6, 1956), affinity-purified polyclonal or fragments thereof (Chao et al., *Res. Comm. in Chem. Path. & Pharm.,* 9: 749–61, 1974).

Monoclonal antibodies useful in the practice of the present invention include whole antibody and fragments thereof. Such monoclonal antibodies and fragments are producible in accordance with conventional techniques, such as hybridoma synthesis, recombinant DNA techniques and protein synthesis. Useful monoclonal antibodies and fragments may be derived from any species (including humans) or may be formed as chimeric proteins which employ sequences from more than one species. See, generally, Kohler and Milstein, *Nature,* 256: 495–97, 1975; *Eur. J. Immunol.,* 6: 511–19, 1976.

Human monoclonal antibodies and "humanized" murine antibodies are also useful as targeting moieties in accordance with the present invention. Human monoclonal antibodies may be obtained from human serum, from hybrid mice or other mammals having a functional human immune system, using hybridoma technology, or the like. Also, a murine monoclonal antibody, for example, may be "humanized" by genetically recombining the nucleotide sequence encoding the murine Fv region (i.e., containing the antigen binding site which antibodies are also known as chimeric antibodies) or the complementarity determining regions thereof with the nucleotide sequence encoding a human constant domain region and an Fc region, e.g., in a manner similar to that disclosed in European Patent Application No. 0,411,893 A2. Some additional murine residues may also be retained within the human variable region framework domains to ensure proper target site binding characteristics. Humanized targeting moieties are recognized to decrease the immunoreactivity of the antibody or polypeptide in the host recipient, permitting an increase in the half-life and a reduction in the possibility of adverse immune reactions.

Types of active agents (diagnostic or therapeutic) useful herein include toxins, drugs, anti-tumor agents, and radionuclides. Several of the potent toxins useful within the present invention consist of an A and a B chain. The A chain is the cytotoxic portion and the B chain is the receptor-binding portion of the intact toxin molecule (holotoxin). Because toxin B chain may mediate non-target cell binding, it is often advantageous to conjugate only the toxin A chain to a targeting protein. However, while elimination of the toxin B chain decreases non-specific cytotoxicity, it also generally leads to decreased potency of the toxin A chain-targeting protein conjugate, as compared to the corresponding holotoxin-targeting protein conjugate.

Preferred toxins in this regard include holotoxins, such as abrin, ricin, modeccin, Pseudomonas exotoxin A, Diphtheria toxin, pertussis toxin and Shiga toxin; and A chain or "A chain-like" molecules, such as ricin A chain, abrin A chain, modeccin A chain, the enzymatic portion of Pseudomonas exotoxin A, Diphtheria toxin A chain, the enzymatic portion of pertussis toxin, the enzymatic portion of Shiga toxin, gelonin, pokeweed antiviral protein, saporin, tritin, barley toxin and snake venom peptides. Ribosomal inactivating proteins (RIPs), naturally occurring protein synthesis inhibitors that lack translocating and cell-binding ability, are also suitable for use herein. Extremely highly toxic toxins, such as palytoxin and the like, are also contemplated for use in the practice of the present invention.

Charge modification of proteinaceous targeting moieties and conjugates containing such targeting moieties and diagnostically or therapeutically active agents is discussed in published European Patent Application No. EP 329,184. Preferred charge modification in accordance with the present invention involves treatment of a proteinaceous active agent with a anion-forming reagent to provide a charge-modified moiety or conjugate exhibiting an acidic shift in isoelectric point. Preferably, the shift in isoelectric point is one-tenth of a pH unit or greater. Generally, charge-modified proteins exhibit a serum half-life that is at least 10% greater than the half-life of native proteins. A 50% or greater increase in half-life is not uncommon following charge modification to a protein.

Anion-forming agents useful in the practice of the present invention are structured to react with functional groups of the protein to be charge-modified and incorporate a negatively charged group to impart an acidic shift in the pI of the protein to be charge-modified. Preferred anion-forming agents useful in the practice of the present invention are structured to react with primary amines on lysine residues of the protein to be charge modified. Such anion-forming agents include active esters (carboxylic and imide), maleimides and anhydrides. Preferred active esters include N-hydroxysuccinimidyl, thiophenyl, 2,3,5,6-tetrafluorophenyl, and 2,3,5,6,-tetrafluorothiophenyl esters. Derivatization of other protein residues may also be employed in the practice of the present invention (e.g., derivatization of arginine residues with glyoxal, phenyl glyoxal or cyclohexanedione). Negatively charged groups which may be used to impart an acidic shift to proteinaceous active agents include phosphates, phosphonates, sulfates, nitrates, borates, silicates, carbonates, and carboxyl groups such as native carboxyl groups or carboxyl groups generated from an anhydride during the reaction of the anion-forming agent with the protein.

Useful anion-forming agents include compounds incorporating an anhydride and/or at least one COOH group, such as succinic anhydride, other cyclic acid anhydrides, phthalic anhydride, maleic anhydride, N-ethyl maleimide substituted with carboxyl groups, aliphatic anhydrides (e.g., acetic anhydride), aromatic anhydrides, pH-reversible anhydrides (e.g., citraconic anhydride and dimethyl maleic anhydride), alpha halo acids such as bromoacetate and iodoacetate, and diacids or triacids substituted with a functional group that reacts with an amino acid on a protein to be charge-modified.

For example, succinic anhydride is dissolved in DMSO or another dry organic solvent at a concentration of 40 mg per 200 microliters. This succinic anhydride solution (or a dilution thereof up to 2.5 ml in anhydrous DMSO, $1.73\times10^{-2}$M) is added to a protein (e.g., holotoxin or toxin domain or conjugate containing one or more of these components) solution (e.g., 3–5 mg/ml in carbonate/bicarbonate buffer, pH 8.5–9.0) at molar ratios of succinic anhydride to protein of 1:5, 1:10 and 1:25 (with higher molar ratios preferred). The reaction is carried out at room temperature for 15–30 minutes. After reaction completion, succinic acid is removed by ultrafiltration or by gel filtration. The degree of isoelectric shift is determined by isoelectric focusing. The toxicity of charge-modified active agents is tested in accordance with known procedures for toxicity testing.

Preferred drugs suitable for use herein include conventional chemotherapeutics, such as vinblastine, doxorubicin, bleomycin, methotrexate, 5-fluorouracil, 6-thioguanine, cytarabine, cyclophosphamide and cis-platinum, as well as other conventional chemotherapeutics as described in *Cancer: Principles and Practice of Oncology,* 2d ed., V. T. DeVita, Jr., S. Hellman, S. A. Rosenberg, J.B. Lippincott Co., Philadelphia, Pa., 1985, Chapter 14. A particularly preferred drug within the present invention is a trichothecene.

Trichothecenes are drugs produced by soil fungi of the class *Fungi imperfecti* or isolated from *Baccharus megapotamica* (Bamburg, J. R. *Proc. Molec. Subcell. Biol.* 8:41–110, 1983; Jarvis & Mazzola, *Acc. Chem. Res.* 15:338–395, 1982). They appear to be the most toxic molecules that contain only carbon, hydrogen and oxygen (Tamm, C. *Fortschr. Chem. Org. Naturst.* 31:61–117, 1974). They are all reported to act at the level of the ribosome as inhibitors of protein synthesis at the initiation, elongation, or termination phases.

There are two broad classes of trichothecenes: those that have only a central sesquiterpenoid structure and those that have an additional macrocyclic ring (simple and macrocyclic trichothecenes, respectively). The simple trichothecenes may be subdivided into three groups (i.e., Group A, B, and C) as described in U.S. Pat. Nos. 4,744,981 and 4,906,452 (incorporated herein by reference). Representative examples of Group A simple trichothecenes include: Scirpene, Roridin C, dihydrotrichothecene, Scirpen-4, 8-diol, Verrucarol, Scirpentriol, T-2 tetraol, pentahydroxyscirpene, 4-deacetylneosolaniol, trichodermin, deacetylcalonectrin, calonectrin, diacetylverrucarol, 4-monoacetoxyscirpenol, 4,15-diacetoxyscirpenol, 7-hydroxydiacetoxyscirpenol, 8-hydroxydiacetoxy-scirpenol (Neosolaniol), 7,8-dihydroxydiacetoxyscirpenol, 7-hydroxy-8-acetyldiacetoxyscirpenol, 8-acetylneosolaniol, NT-1, NT-2, HT-2, T-2, and acetyl T-2 toxin. Representative examples of Group B simple trichothecenes include: Trichothecolone, Trichothecin, deoxynivalenol, 3-acetyldeoxynivalenol, 5-acetyldeoxynivalenol, 3,15-diacetyldeoxynivalenol, Nivalenol, 4-acetylnivalenol (Fusarenon-X), 4,15-idacetylnivalenol, 4,7,15-triacetylnivalenol, and tetra-acetylnivalenol. Representative examples of Group C simple trichothecenes include: Crotocol and Crotocin. Representative macrocyclic trichothecenes include Verrucarin A, Verrucarin B, Verrucarin J (Satratoxin C), Roridin A, Roridin D, Roridin E (Satratoxin D), Roridin H, Satratoxin F, Satratoxin G, Satratoxin H, Vertisporin, Mytoxin A, Mytoxin C, Mytoxin B, Myrotoxin A, Myrotoxin B, Myrotoxin C, Myrotoxin D, Roritoxin A, Roritoxin B, and Roritoxin D. In addition, the general "trichothecene" sesquiterpenoid ring structure is also present in compounds termed "baccharins" isolated from the higher plant *Baccharis megapotamica,* and these are described in the literature, for instance as disclosed by Jarvis et al. (Chemistry of Alleopathy, ACS Symposium Series No. 268: ed. A. C. Thompson, 1984, pp. 149–159).

Experimental drugs, such as mercaptopurine, N-methylformamide, 2-amino-1,3,4-thiadiazole, melphalan, hexamethylmelamine, gallium nitrate, 3% thymidine, dichloromethotrexate, mitoguazone, suramin, bromodeoxyuridine, iododeoxyuridine, semustine, 1-(2-chloroethyl)-3-(2,6-dioxo-3-piperidyl)-1-nitrosourea, N,N'-hexamethylene-bis-acetamide, azacitidine, dibromodulcitol, Erwinia asparaginase, ifosfamide, 2-mercaptoethane sulfonate, teniposide, taxol, 3-deazauridine, soluble Baker's antifol, homoharringtonine, cyclocytidine, acivicin, ICRF-187, spiromustine, levamisole, chlorozotocin, aziridinyl benzoquinone, spirogermanium, aclarubicin, pentostatin, PALA, carboplatin, amsacrine, caracemide, iproplatin, misonidazole, dihydro-5-azacytidine, 4'-deoxy-doxorubicin, menogaril, triciribine phosphate, fazarabine, tiazofurin, teroxirone, ethiofos, N-(2-hydroxyethyl)-2-nitro-1H-imidazole-1-acetamide, mitoxantrone, acodazole, amonafide, fludarabine phosphate, pibenzimol, didemnin B, merbarone, dihydrolenperone, flavone-8-acetic acid, oxantrazole, ipomeanol, trimetrexate, deoxyspergualin, echinomycin, and dideoxycytidine (see *NCI Investigational Drugs, Pharmaceutical Data* 1987, NIH Publication No. 88-2141, Revised November 1987) are also preferred.

Radionuclides useful within the present invention include gamma-emitters, positron-emitters, Auger electron-emitters, X-ray emitters and fluorescence-emitters, with beta- or alpha-emitters preferred for therapeutic use. Radionuclides are well-known in the art and include $^{123}I$, $^{125}I$, $^{130}I$, $^{131}I$, $^{133}I$, $^{135}I$, $^{47}Sc$, $^{72}As$, $^{72}Se$, $^{90}Y$, $^{88}Y$, $^{97}Ru$, $^{100}Pd$, $^{101m}Rh$, $^{119}Sb$, $^{128}Ba$, $^{197}Hg$, $^{211}At$, $^{212}Bi$, $^{153}Sm$, $^{169}Eu$, $^{212}Pb$, $^{109}Pd$, $^{111}In$, $^{67}Ga$, $^{68}Ga$, $^{67}Cu$, $^{75}Br$, $^{76}Br$, $^{77}Br$, $^{99m}Tc$, $^{11}C$, $^{13}N$, $^{15}O$ and $^{18}F$. Preferred therapeutic radionuclides include $^{188}Re$, $^{186}Re$, $^{203}Pb$, $^{212}Pb$, $^{212}Bi$, $^{109}Pd$, $^{64}Cu$, $^{67}Cu$, $^{90}Y$, $^{125}I$, $^{131}I$, $^{77}Br$, $^{211}At$, $^{97}Ru$, $^{105}Rh$, $^{198}Au$, $^{177}Lu$ and $^{199}Ag$.

Other anti-tumor agents, e.g., agents active against proliferating cells, are administrable in accordance with the present invention. Exemplary anti-tumor agents include cytokines, such as IL-2, tumor necrosis factor or the like, lectin inflammatory response promoters (selectins), such as L-selectin, E-selectin, P-selectin or the like, and like molecules.

Ligands suitable for use within the present invention include biotin, haptens, lectins, epitopes, dsDNA fragments, enzyme inhibitors and analogs and derivatives thereof. Useful complementary anti-ligands include avidin (for biotin), carbohydrates (for lectins), antibody, fragments or analogs thereof, including mimetics (for haptens and epitopes), zinc finger proteins (for dsDNA fragments) and enzymes (for enzyme inhibitors. Preferred ligands and anti-ligands bind to each other with an affinity of at least about $k_D \geqq 10^{-9}$M.

The 1,4,7,10-tetraazacyclododecane-N,N',N'',N'''-tetra acetic acid (DOTA)-biotin conjugate (DOTA-LC-biotin) depicted below has been reported to have desirable in vivo biodistribution and is cleared primarily by renal excretion.

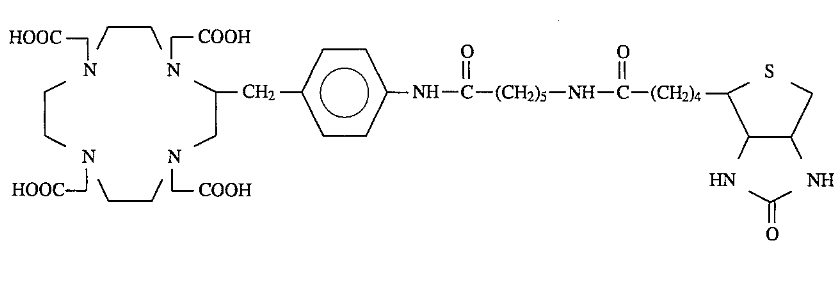

DOTA may also be conjugated to other ligands or to anti-ligands in the practice of the present invention.

Because DOTA strongly binds Y-90 and other radionuclides, it has been proposed for use in radioimmunotherapy. For therapy, it is very important that the radionuclide be stably bound within the DOTA chelate and that the DOTA chelate be stably attached to a ligand or anti-ligand. For illustrative purposes, DOTA-biotin conjugates are described. Only radiolabeled DOTA-biotin conjugates exhibiting those two characteristics are useful to deliver radionuclides to the targets. Release of the radionuclide from the DOTA chelate or cleavage of the biotin and DOTA conjugate components in serum or at non-target sites renders the conjugate unsuitable for use in therapy.

Serum stability of DOTA-LC-biotin (where LC refers to the "long chain" linker, including an aminocaproyl spacer between the biotin and the DOTA conjugate components) shown above, while reported in the literature to be good, has proven to be problematic. Experimentation has revealed that DOTA-LC-biotin is rapidly cleared from the blood and excreted into the urine as fragments, wherein the biotinamide bond rather than the DOTA-amide bond has been cleaved, as shown below.

Cleavage of the benzamide was not observed as evidenced by the absence of detectable quantities of iodobenzoic acid in the serum.

It appears that the cleavage results from the action of serum biotinidase. Biotinidase is a hydrolytic enzyme that catalyzes the cleavage of biotin from biotinyl peptides. See, for example, Evangelatos, et al., "Biotinidase Radioassay Using an I-125-Biotin Derivative, Avidin, and Polyethylene Glycol Reagents," *Analytical Biochemistry*, 196: 385–89, 1991.

Drug-biotin conjugates which structurally resemble biotinyl peptides are potential substrates for cleavage by plasma biotinidase. Poor in vivo stability therefore limits the use of drug-biotin conjugates in therapeutic applications. The use of peptide surrogates to overcome poor stability of peptide therapeutic agents has been an area of intense research effort. See, for example, Spatola, Peptide Backbone Modification: A Structure-Activity Analysis of Peptide Containing Amide Bond Surrogates, "*Chemistry and Biochemistry of Amino Acids, Peptides and Proteins,*" vol. 7, Weinstein, ed., Marcel Dekker, New York, 1983; and Kim et al., "A New Peptide Bond Surrogate: 2-Isoxazoline in Pseudodipeptide Chemistry," *Tetrahedron Letters*, 45: 6811–14, 1991.

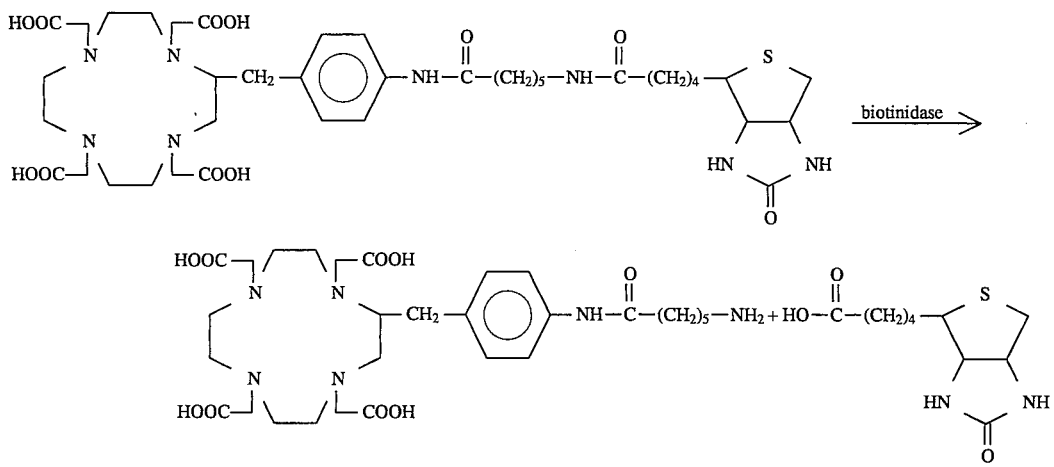

Additional experimentation employing PIP-biocytin conjugates produced parallel results as shown below.

Elimination of the aminocaproyl spacer of DOTA-LC-biotin gives DOTA-SC-biotin (where the SC indicates the

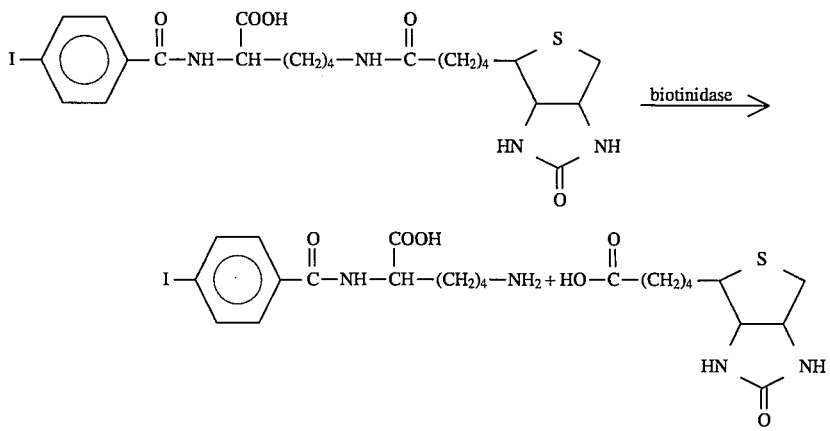

"short chain" linker between the DOTA and biotin conjugate components), which molecule is shown below:

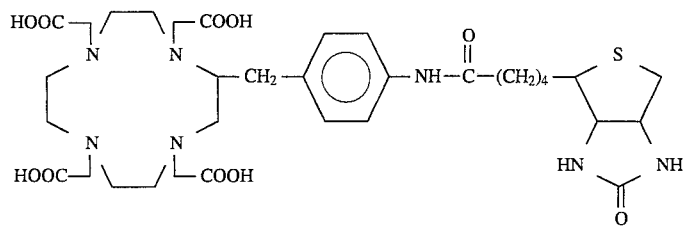

DOTA-SC-biotin exhibits significantly improved serum stability in comparison to DOTA-LC-biotin. This result does not appear to be explainable on the basis of biotinidase activity alone. The experimentation leading to this conclusion is summarized in the Table set forth below.

Time Dependent Cleavage of DOTA-Biotin conjugates

| | % Avidin Binding | | |
|---|---|---|---|
| Time at 37° C. | PIP-Biocytin | Y-90-LC DOTA-Biotin | Y-90-SC DOTA-Biotin |
| 5 Minutes | 75% | 50% | — |
| 15 Minutes | 57% | 14% | — |
| 30 Minutes | 31% | 12% | — |
| 60 Minutes | — | 0% | 98% |
| 20 Hours | — | 0% | 60% | where "—" indicates that the value was not measured.

The difference in serum stability between DOTA-LC-biotin and DOTA-SC-biotin might be explained by the fact that the SC derivative contains an aromatic amide linkage in contrast to the aliphatic amide linkage of the LC derivative, with the aliphatic amide linkage being more readily recognized by enzymes as a substrate therefor. This argument cannot apply to biotinidase, however, because biotinidase very efficiently cleaves aromatic amides. In fact, it is recognized that the simplest and most commonly employed biotinidase activity measuring method uses N-(d-biotinyl)-4-aminobenzoate (BPABA) as a substrate, with the hydrolysis of BPABA resulting in the liberation of biotin and 4-aminobenzoate (PABA). See, for example, B. Wolf, et al., "Methods in Enzymology," pp. 103–111, Academic Press Inc., 1990. Consequently, one would predict that DOTA-SC-biotin, like its LC counterpart, would be a biotinidase substrate. Since DOTA-SC-biotin exhibits serum stability, biotinidase activity alone does not adequately explain why some conjugates are serum stable while others are not, A series of DOTA-biotin conjugates was therefore synthesized by the present inventors to determine which structural features conferred serum stability to the conjugates.

Some general strategies for improving serum stability of peptides with respect to enzymatic action are the following: incorporation of D-amino acids, N-methyl amino acids and alpha-substituted amino acids.

In vivo stable biotin-DOTA conjugates are useful within the practice of the present invention. In vivo stability imparts the following advantages:

1) increased tumor uptake in that more of the radioisotope will be targeted to the previously localized targeting moiety-streptavidin; and 2) increased tumor retention, if biotin is more stably bound to the radioisotope.

In addition, the linkage between DOTA and biotin may also have a significant impact on biodistribution (including normal organ uptake, target uptake and the like) and pharmacokinetics.

The strategy for design of the DOTA-containing molecules and conjugates of the present invention involved three primary considerations:

1) in vivo stability (including biotinidase and general peptidase activity resistance), with an initial acceptance criterion of 100% stability for 1 hour;
2) renal excretion; and
3) ease of synthesis.

The DOTA-biotin conjugates of the present invention reflect the implementation of one or more of the following strategies:

1) substitution of the carbon adjacent to the cleavage susceptible amide nitrogen;
2) alkylation of the cleavage susceptible amide nitrogen;
3) substitution of the amide carbonyl with an alkyl amino group;
4) incorporation of D-amino acids as well as analogs or derivatives thereof; or
5) incorporation of thiourea linkages.

DOTA-biotin conjugates in accordance with the present invention may be generally characterized as follows: conjugates that retain the biotin carboxy group in the structure thereof and those that do not (i.e., the terminal carboxy group of biotin has been reduced or otherwise chemically modified. Structures of such conjugates represented by the following general formula have been devised:

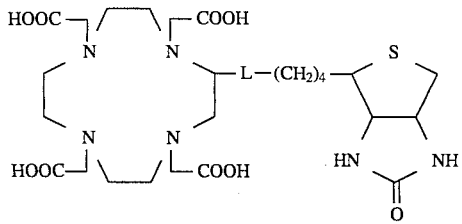

wherein L may alternatively be substituted in one of the following ways on one of the —CH$_2$—COOH branches of the DOTA structure: —CH(L)—COOH or —CH$_2$COOL or —CH$_2$COL). When these alternative structures are employed, the portion of the linker bearing the functional group for binding with the DOTA conjugate component is selected for the capability to interact with either the carbon or the carboxy in the branch portions of the DOTA structure, with the serum stability conferring portion of the linker structure being selected as described below.

In the case where the linkage is formed on the core of the DOTA structure as shown above, L is selected according to the following principles, with the portion of the linker designed to bind to the DOTA conjugate component selected for the capability to bind to an amine.

A. One embodiment of the present invention includes linkers incorporating a D-amino acid spacer between a DOTA aniline amine and the biotin carboxy group shown above. Substituted amino acids are preferred for these embodiments of the present invention, because alpha-substitution also confers enzymatic cleavage resistance. Exemplary L moieties of this embodiment of the present invention may be represented as follows:

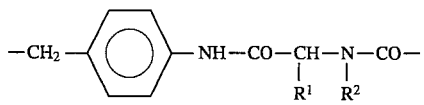

where $R^1$ is selected from lower alkyl, lower alkyl substituted with hydrophilic groups (preferably, $(CH_2)_n$—OH, $(CH_2)_n$—$OSO_3$, $(CH_2)_n$—$SO_3$, $$(CH_2)_n-\underset{\underset{O}{\|}}{\overset{\overset{OH}{|}}{O}P}OH,$$

where n is 1 or 2), glucuronide-substituted amino acids or other glucuronide derivatives; and $R^2$ is selected from hydrogen, lower alkyl, substituted lower alkyl (e.g., hydroxy, sulfate, phosphonate or a hydrophilic moiety (preferably OH).

For the purposes of the present disclosure, the term "lower alkyl" indicates an alkyl group with from one to five carbon atoms. Also, the term "substituted" includes one or several substituent groups, with a single substituent group preferred.

Preferred L groups of this embodiment of the present invention include the following:

$R^1$=$CH_3$ and $R^2$=H (a D-alanine derivative, with a synthetic scheme therefor shown in Example XI); p1 $R^1$=$CH_3$ and $R^2$=$CH_3$ (an N-methyl-D-alanine derivative);

$R^1$=$CH_2$—OH and $R^2$=H (a D-serine derivative);

$R^1$=$CH_2OSO_3$ and $R^2$=H (a D-serine-O-sulfate-derivative); and

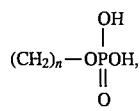

and $R^2$=H (a D-serine-O-phosphonate-derivative);

Other preferred moieties of this embodiment of the present invention include molecules wherein $R^1$ is hydrogen and $R^2$=—$(CH_2)_n$OH or a sulfate or phosphonate derivative thereof and n is 1 or 2 as well as molecules wherein $R^1$ is

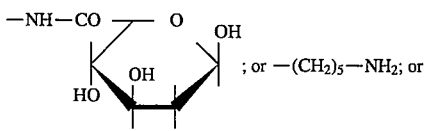

; or —$(CH_2)_5$—$NH_2$; or

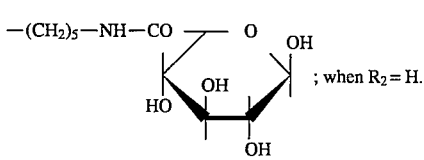

; when $R_2$ = H.

Preferred moieties incorporating the glucuronide of D-lysine and the glucuronide of amino pimelate are shown below as I and II, respectively.

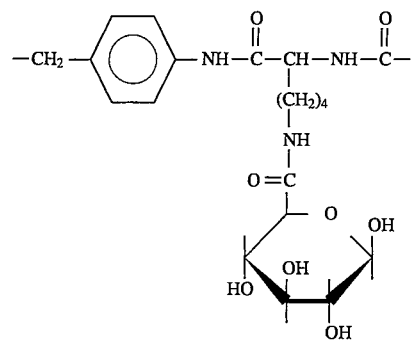

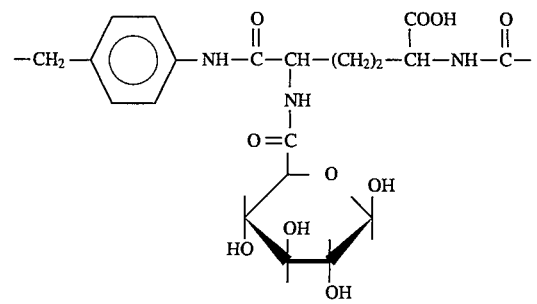

A particularly preferred linker of this embodiment of the present invention is the D-alanine derivative set forth above.

B. Linkers incorporating alkyl substitution on one or more amide nitrogen atoms are also encompassed by the present invention, with some embodiments of such linkers preparable from L-amino acids. Amide bonds having a substituted amine moiety are less susceptible to enzymatic cleavage. Such linkers exhibit the following general formula:

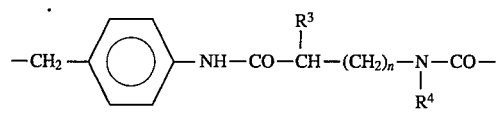

where $R^4$ is selected from hydrogen, lower alkyl, lower alkyl substituted with hydroxy, sulfate, phosphonate or the like and

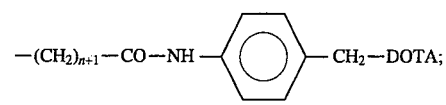

$R^3$ is selected from hydrogen; an amine; lower alkyl; an amino- or a hydroxy-, sulfate- or phosphonate-substituted lower alkyl; a glucuronide or a glucuronide-derivatized amino groups; and n ranges from 0–4.

Preferred linkers of this embodiment of the present invention include:

$R^3$=H and $R^4$=$CH_3$ when n=4, synthesizable as discussed in Example XI;

$R^3$=H and $R^4$=$CH_3$ when n=0, synthesizable from N-methyl-glycine (having a trivial name of sarcosine) as described in Example XI;

$R^3$=$NH_2$ and $R^4$=$CH_3$, when n=0;

$R^3$=H and

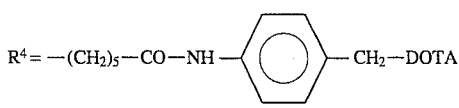

when n=4 (Bis-DOTA-LC-biotin), synthesizable bromohexanoic acid as discussed in Example XI; and
$R^3$=H and

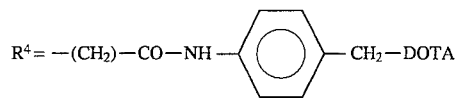

when n=0 (bis-DOTA-SC-biotin), synthesizable from iminodiacetic acid.

The synthesis of a conjugate including a linker wherein $R^3$ is H and $R^4$ is —$CH_2CH_2OH$ and n is 0 is also described in Example XI. Schematically, the synthesis of a conjugate of this embodiment of the present invention wherein n is 0, $R^3$ is H and $R^4$ is —$CH_2$—COOH is shown below.

2) substitution of the amide nitrogen adjacent to the biotin carboxyl group blocks peptide and/or biotinidase cleavage at that site.

Bis-DOTA-LC-biotin, the glycine-based linker and the N-methylated linker where $R^3$=H, $R^4$=$CH_3$, n=4 are particularly preferred linkers of this embodiment of the present invention.

C. Another linker embodiment incorporates a thiourea moiety therein. Exemplary thiourea adducts of the present invention exhibit the following general formula:

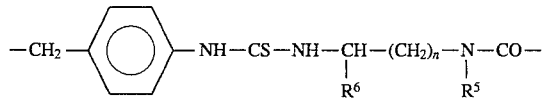

where $R^5$ is selected from hydrogen or lower alkyl;
$R^6$ is selected from H and a hydrophilic moiety; and
n ranges from 0–4.

Preferred linkers of this embodiment of the present invention are as follows:
$R^5$=H and $R^6$=H when n=5;
$R^5$=H and $R^6$=COOH when n=5; and

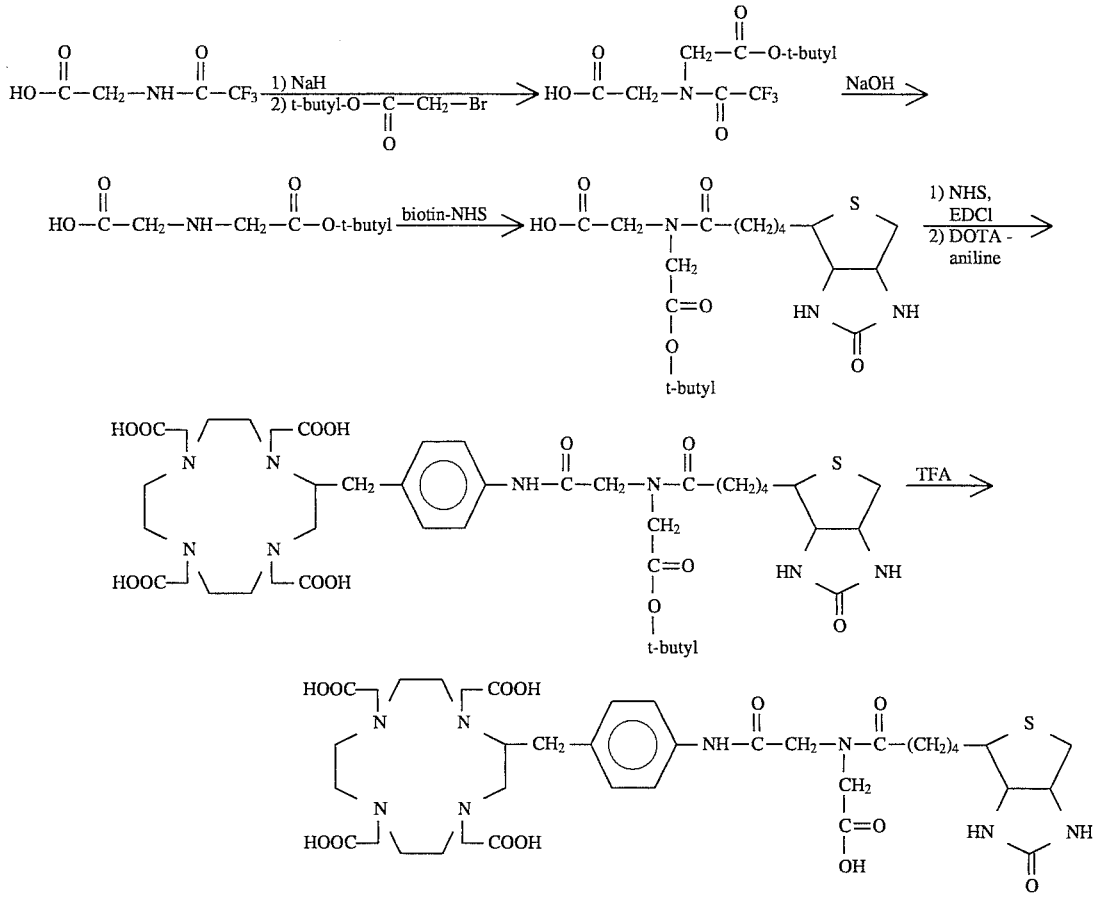

Bis-DOTA-LC-biotin, for example, offers the following advantages:

1) incorporation of two DOTA molecules on one biotin moiety increases the overall hydrophilicity of the biotin conjugate and thereby directs in vivo distribution to urinary excretion; and $R^5$=$CH_3$ and $R^6$=COOH when n=5.

The second preferred linker recited above can be prepared using either L-lysine or D-lysine. Similarly, the third preferred linker can be prepared using either N-methyl-D-lysine or N-methyl-L-lysine.

Another thiourea adduct of minimized lipophilicity is

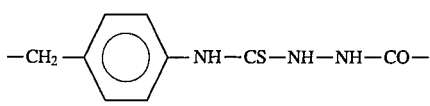

which may be formed via the addition of biotinhydrazide (commercially available from Sigma Chemical Co., St. Louis, Mo.) and DOTA-benzyl-isothiocyanate (a known compound synthesized in one step from DOTA-aniline), with the thiourea-containing compound formed as shown below.

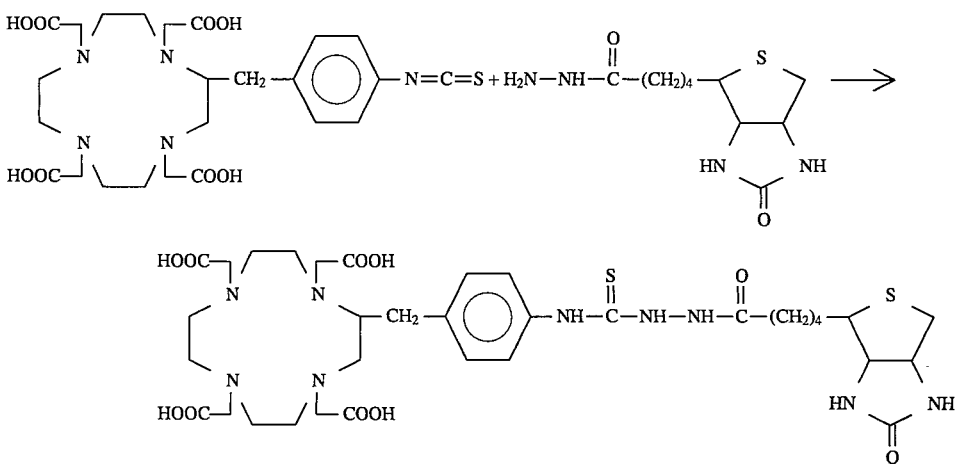

D. Amino acid-derived linkers of the present invention with substitution of the carbon adjacent to the cleavage susceptible amide have the general formula set forth below:

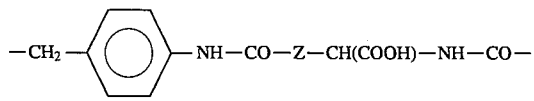

wherein Z is —$(CH_2)_2$—, conveniently synthesized form glutamic acid; or

Z=—$CH_2$—S—$CH_2$—, synthesizable from cysteine and iodo-acetic acid; or

Z=—$CH_2$—, conveniently synthesized form aspartic acid; or

Z=—$(CH_2)_n$—CO—O—$CH_2$—, where n ranges from 1–4 and which is synthesizable from serine.

E. Another exemplary linker embodiment of the present invention has the general formula set forth below:

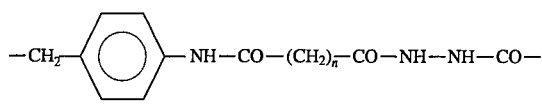

and n ranges from 1–5.

F. Another embodiment involves disulfide-containing linkers, which provide a metabolically cleavable moiety (—S—S—) to reduce non-target retention of the biotin-DOTA conjugate. Exemplary linkers of this type exhibit the following formula:

$$-CH_2-\bigcirc-NH-CO-(CH_2)_n-S-S-(CH_2)_{n'}-NH-CO-$$

n and n' preferably range between 0 and 5.

The advantage of using conditionally cleavable linkers is an improvement in target/non-target localization of the active agent. Conditionally cleavable linkers include enzymatically cleavable linkers, linkers that are cleaved under acidic conditions, linkers that are cleaved under basic conditions and the like. More specifically, use of linkers that are cleaved by enzymes, which are present in non-target tissues but reduced in amount or absent in target tissue, can increase target cell retention of active agent relative to non-target cell retention. Such conditionally cleavable linkers are useful, for example, in delivering therapeutic radionuclides to target cells, because such active agents do not require internalization for efficacy, provided that the linker is stable at the target cell surface or protected from target cell degradation.

Cleavable linkers are also useful to effect target site selective release of active agent at target sites. Active agents that are preferred for cleavable linker embodiments of the present invention are those that are substantially non-cytotoxic when conjugated to ligand or anti-ligand. Such active agents therefore require release from the ligand- or anti-ligand-containing conjugate to gain full potency. For example, such active agents, while conjugated, may be unable to bind to a cell surface receptor; unable to internalize either actively or passively; or unable to serve as a binding substrate for a soluble (intra- or inter-cellular) binding protein or enzyme. Exemplary of an active agent-containing conjugate of this type is chemotherapeutic drug-cis-aconityl-biotin. The cis-aconityl linker is acid sensitive. Other acid sensitive linkers useful in cleavable linker embodiments of the present invention include esters, thioesters and the like. Use of conjugates wherein an active agent and a ligand or an anti-ligand are joined by a cleavable linker will result in the selective release of the active agent at tumor cell target sites, for example, because the inter-cellular millieu of tumor tissue is generally of a lower pH (more highly acidic) than the inter-cellular milieu of normal tissue.

G. Ether, thioether, ester and thioester linkers are also useful in the practice of the present invention. Ether and thioether linkers are stable to acid and basic conditions and are therefore useful to deliver active agents that are potent in conjugated form, such as radionuclides and the like. Ester and thioesters are hydrolytically cleaved under acidic or basic conditions or are cleavable by enzymes including esterases, and therefore facilitate improved target:non-target retention. Exemplary linkers of this type have the following general formula:

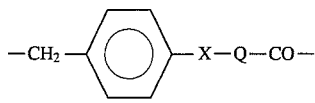

X is O or S; and
Q is a bond, a methylene group, a —CO— group or —CO—$(CH_2)_n$—NH—; and
n ranges from 1–5.

Other such linkers have the general formula:
—$CH_2$—X—Q, where Q and X are defined as set forth above.

H. Another amino-containing linker of the present invention is structured as follows:

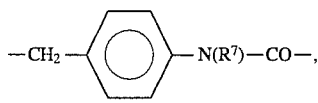

where $R^7$ is lower alkyl, preferably methyl.
In this case, resistance to enzymatic cleavage is conferred by the alkyl substitution on the amine.

I. Polymeric linkers are also contemplated by the present invention. Dextran and cyclodextran are preferred polymers useful in this embodiment of the present invention as a result of the hydrophilicity of the polymer, which leads to favorable excretion of conjugates containing the same. Other advantages of using dextran polymers are that such polymers are substantially non-toxic and non-immunogenic, that they are commercially available in a variety of sizes and that they are easy to conjugate to other relevant molecules. Also, dextran-linked conjugates exhibit advantages when non-target sites are accessible to dextranase, an enzyme capable of cleaving dextran polymers into smaller units while non-target sites are not so accessible.

Other linkers of the present invention are produced prior to conjugation to DOTA and following the reduction of the biotin carboxy moiety. These linkers of the present invention have the following general formula:

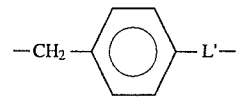

Embodiments of linkers of this aspect of the present invention include the following:

J. An ether linkage as shown below may be formed in a DOTA-biotin conjugate in accordance with the procedure indicated below.

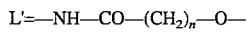

L'=—NH—CO—$(CH_2)_n$—O— where n ranges from 1 to 5, with 1 preferred.

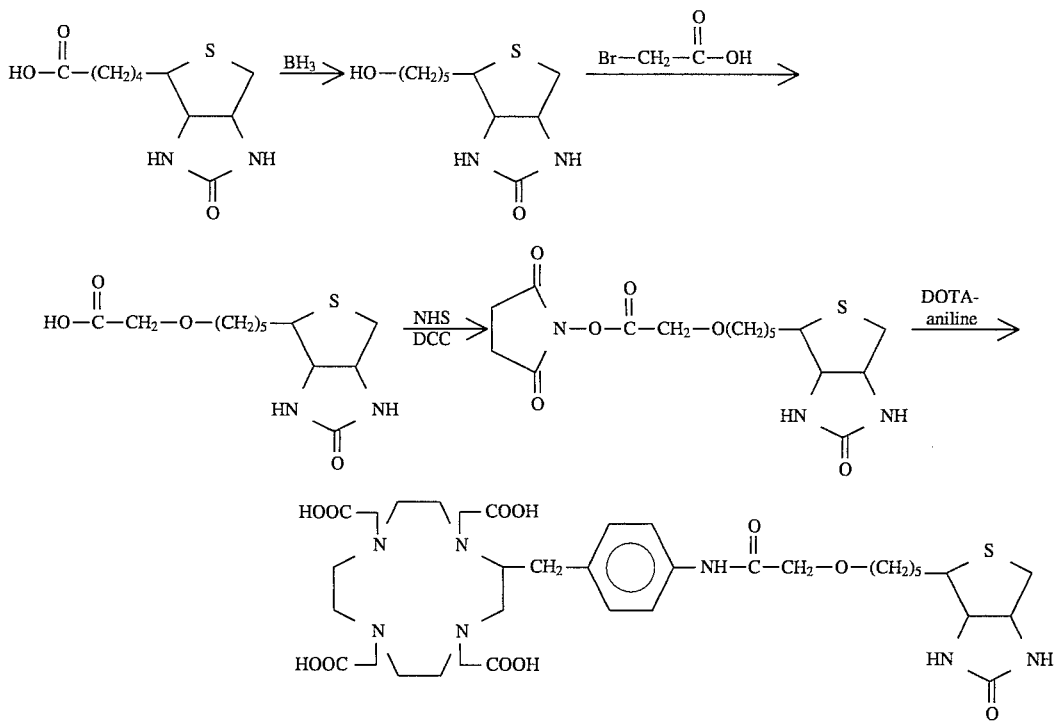

This linker has only one amide moiety which is bound directly to the DOTA aniline (as in the structure of DOTA-SC-biotin). In addition, the ether linkage imparts hydrophilicity, an important factor in facilitating renal excretion.

K. An amine linker formed from reduced biotin (hydroxybiotin or aminobiotin) is shown below, with conjugates containing such a linker formed, for example, in accordance with the procedure described in Example XI.

L'=—NH—

This linker contains no amide moieties and the unalkylated amine may impart favorable biodistribution properties since unalkylated DOTA-aniline displays excellent renal clearance.

L. Substituted amine linkers, which can form conjugates via amino-biotin intermediates, are shown below.

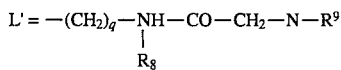

$L' = -(CH_2)_q-NH-CO-CH_2-N-R^9$
                                |
                                $R_8$ where $R^8$ is H; —$(CH_2)_2$—OH or a sulfate or phosphonate derivative thereof; or

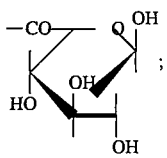

or the like; and $R^9$ is a bond or —$(CH_2)_n$—CO—NH—, where n ranges from 0–5 and is preferably 1 and where q is 0 or 1. These moieties exhibit the advantages of an amide only directly attached to DOTA-aniline and either a non-amide amine imparting a positive charge to the linker in vivo or a N-alkylated glucuronide hydrophilic group, each alternative favoring renal excretion.

M. Amino biotin may also be used as an intermediate in the production of conjugates linked by linkers having favorable properties, such as a thiourea-containing linker of the formula:

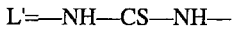

L'=—NH—CS—NH—

Conjugates containing this thiourea linker have the following advantages: no cleavable amide and a short, fairly polar linker which favors renal excretion.

A bis-DOTA derivative of the following formula can also be formed from amino-biotin.

where n ranges from 1 to 5, with 1 and 5 preferred. This molecule offers the advantages of the previously discussed bis-DOTA derivatives with the added advantage of no cleavable amides.

Additional linkers of the present invention which are employed in the production of conjugates characterized by a reduced biotin carboxy moiety are the following:

$L=-(CH_2)_4-NH-$, wherein the amine group is attached to the methylene group corresponding to the reduced biotin carboxy moiety and the methylene chain is attached to a core carbon in the DOTA ring. Such a linker is conveniently synthesizable from lysine.

$L=-(CH_2)_q-CO-NH-$, wherein q is 1 or 2, and wherein the amine group is attached to the methylene group corresponding to the reduced biotin carboxy moiety and the methylene group(s) are attached to a core carbon in the DOTA ring. This moiety is synthesizable from amino-biotin.

The linkers set forth above are useful to produce conjugates having one or more of the following advantages:

bind avidin or streptavidin with the same or substantially similar affinity as free biotin;

bind metal $M^{+3}$ ions efficiently and with high kinetic stability;

are excreted primarily through the kidneys into urine;

are stable to bodily fluid amidases;

penetrate tissue rapidly and bind to pretargeted avidin or streptavidin; and are excreted rapidly with a whole body residence half-life of less than about 5 hours.

Synthetic routes to an intermediate of the DOTA-biotin conjugates depicted above, nitrobenzyl-DOTA, have been proposed. These proposed synthetic routes produce the intermediate compound in suboptimal yield, however. For example, Renn and Meares, "Large Scale Synthesis of Bifunctional Chelating Agent Q-(p-nitrobenzyl)-1,4,7,10-tetraazacyclododecane-N,N',N'',N'''-tetra acetic acid, and the Determination of its Enantiomeric Purity by Chiral Chromatography," *Bioconj. Chem.*, 3: 563–9, 1992, describe a nine-step synthesis of nitrobenzyl-DOTA, including reaction steps that either proceed in low yield or involve cumbersome transformations or purifications. More specifically, the sixth step proceeds in only 26% yield, and the product must be purified by preparative HPLC. Additionally, step eight proceeds in good yield, but the process involves copious volumes of the coreactants.

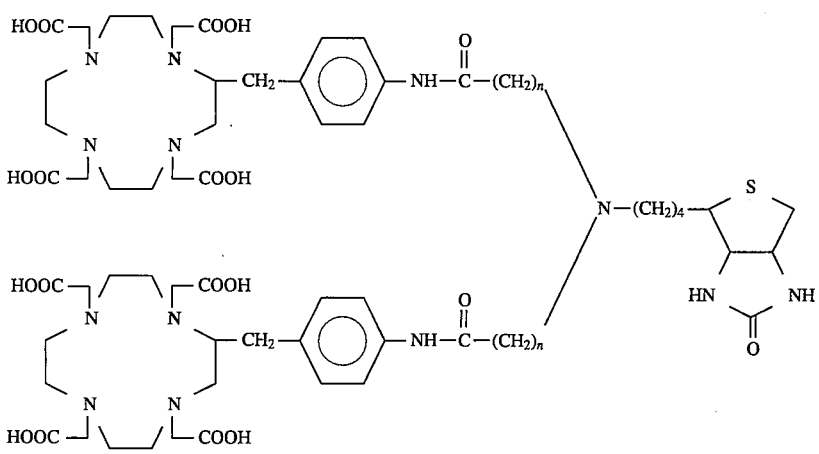

These difficulties in steps 6–8 of the prior art synthesis are overcome in the practice of the present invention through the use of the following synthetic alternative therefor.

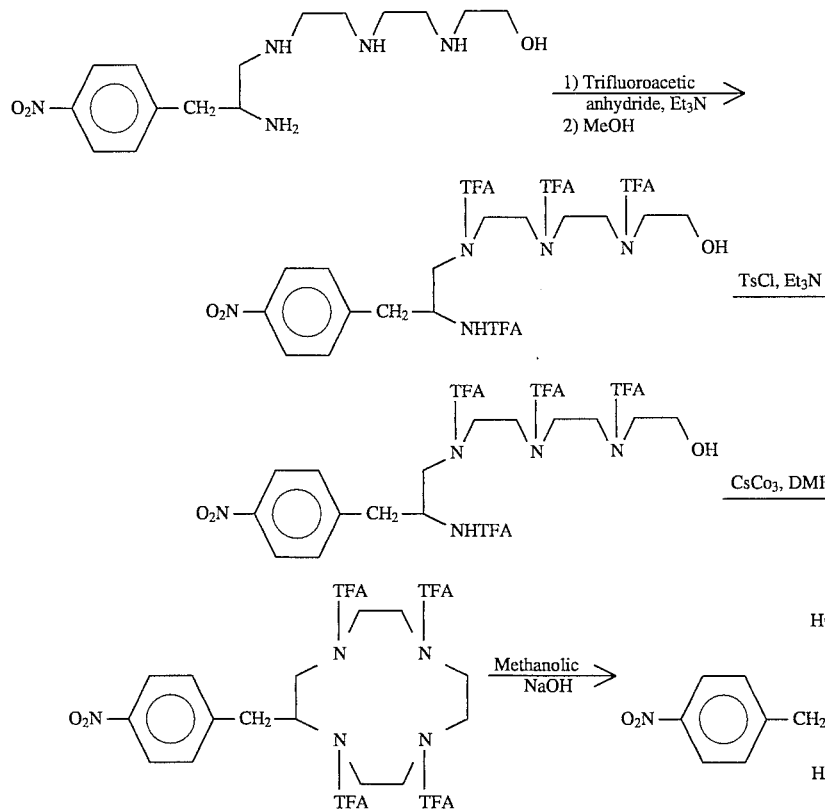

The poor yield in step six of the prior art synthesis procedure, in which a tetra amine alcohol is converted to a tetra-toluenesulfonamide toluenesulfonate as shown below, is the likely result of premature formation of the O-toluenesulfonate functionality (before all of the amine groups have been converted to their corresponding sulfonamides.

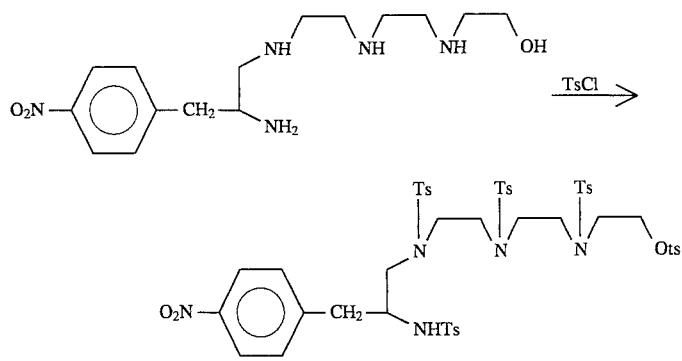

Such a sequence of events would potentially result in unwanted intra- or inter-molecular displacement of the reactive O-toluenesulfonate by unprotected amine groups, thereby generating numerous undesirable side-products.

This problem is overcome in the aforementioned alternative synthesis scheme of the present invention by reacting the tetra-amine alcohol with trifluoroacetic anhydride. Trifluoroacetates, being much poorer leaving groups than toluenesulfonates, are not vulnerable to analogous side reactions. In fact, the easy hydrolysis of trifluoroacetate groups, as reported in Greene and Wuts, "Protecting Groups in Organic Synthesis," John Wiley and Sons, Inc., New York, p. 94, 1991, suggests that addition of methanol to the reaction mixture following consumption of all amines should afford the tetra-fluoroacetamide alcohol as a substantially exclusive product. Conversion of the tetra-fluoroacetamide alcohol to the corresponding toluenesulfonate provides a material which is expected to cyclize analogously to the tetra-toluenesulfonamide toluenesulfonate of the prior art. The cyclic tetraamide product of the cyclization of the toluenesulfonate of tetra-fluoroacetamide alcohol, in methanolic sodium hydroxide at 15°–25° C. for 1 hour, should afford nitro-benzyl-DOTA as a substantially exclusive product. As a result, the use of trifluoracetamide protecting groups circumvents the difficulties associated with cleavage of the very stable toluenesulfonamide protecting group, which involves heating with a large excess of sulfuric acid followed by neutralization with copious volumes of barium hydroxide.

Another alternative route to nitro-benzyl-DOTA is shown below.

route published by Gansow et al., U.S. Pat. No. 4,923,985, because the crucial cyclization step is intramolecular rather than intermolecular. Intramolecular reactions typically proceed in higher yield and do not require high dilution techniques necessary for successful intermolecular reactions.

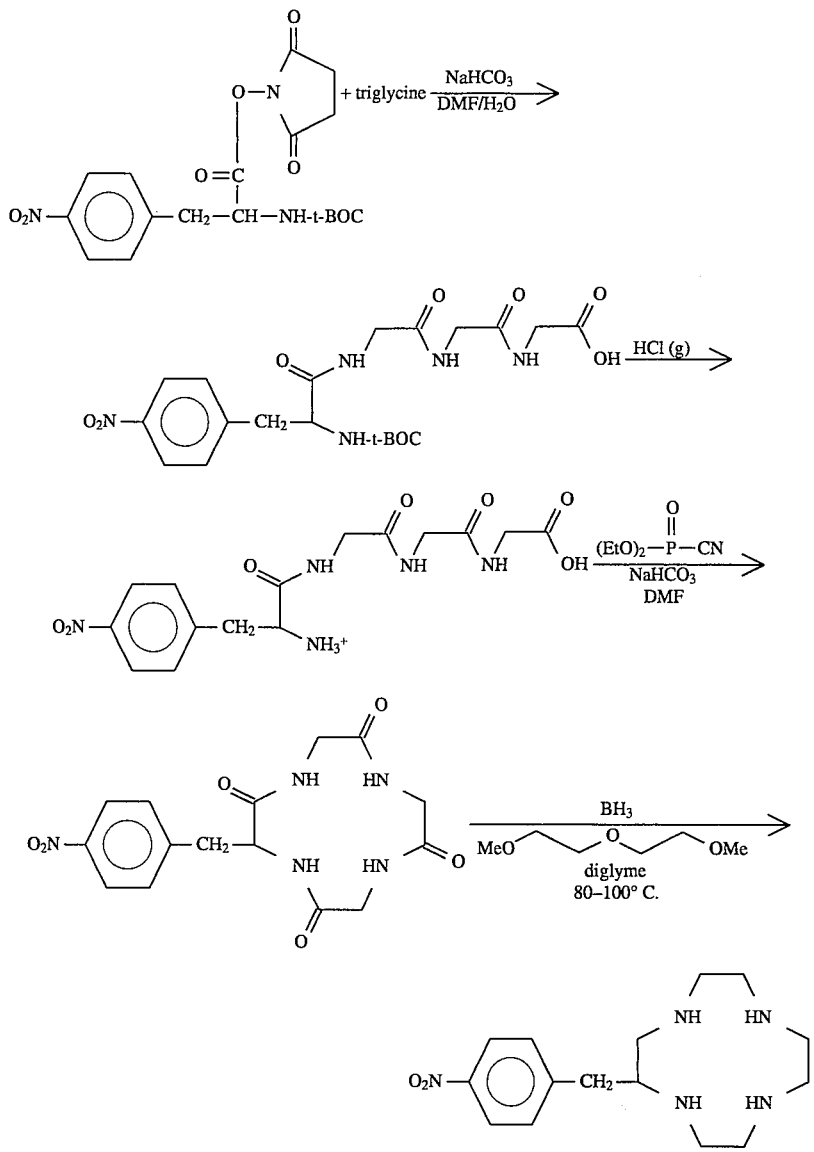

This alternative procedure involves the cyclizaton of p-nitrophenylalanyltriglycine using a coupling agent, such as diethylycyanophosphate, to give the cyclic tetraamide. Subsequent borane reduction provides 2-(p-nitrobenzyl)-1,4,7,10-tetraazacyclododecane, a common precursor used in published routes to DOTA including the Renn and Meares article referenced above. This alternative procedure of the present invention offers a synthetic pathway that is considerably shorter than the prior art Renn and Meares route, requiring two rather than four steps between p-nitrophenylalanyltriglycine to the tetraamine. The procedure of the present invention also avoids the use of tosyl amino protecting groups, which were prepared in low yield and required stringent conditions for removal. Also, the procedure of the present invention poses advantages over the An additional aspect of the present invention is directed to the use of targeting moieties that are monoclonal antibodies or fragments thereof that localize to an antigen that is recognized by the antibody NR-LU-10. Such monoclonal antibodies or fragments may be murine or of other non-human mammalian origin, chimeric, humanized or human.

NR-LU-10 is a 150 kilodalton molecular weight IgG2b monoclonal antibody that recognizes an approximately 40 kilodalton glycoprotein antigen expressed on most carcinomas. In vivo studies in mice using an antibody specific for the NR-LU-10 antigen revealed that such antibody was not rapidly internalized, which would have prevented localization of the subsequently administered active-agent-containing conjugate to the target site.

NR-LU-10 is a well characterized pancarcinoma antibody that has been safely administered to over 565 patients in human clinical trials. The hybridoma secreting NR-LU-10 was developed by fusing mouse splenocytes immunized with intact cells of a human small cell lung carcinoma with P3×63/Ag8UI murine myeloma cells. After establishing a seed lot, the hybridoma was grown via in vitro cell culture methods, purified and verified for purity and sterility.

Radioimmunoassays, immunoprecipitation and Fluorescence-Activated Cell Sorter (FACS) analysis were used to obtain reactivity profiles of NR-LU-10. The NR-LU-10 target antigen was present on either fixed cultured cells or in detergent extracts of various types of cancer cells. For example, the NR-LU-10 antigen is found in small cell lung, non-small cell lung, colon, breast, renal, ovarian, pancreatic, and other carcinoma tissues. Tumor reactivity of the NR-LU-10 antibody is set forth in Table A, while NR-LU- 10 reactivity with normal tissues is set forth in Table B. The values in Table B are obtained as described below. Positive NR-LU-10 tissue reactivity indicates NR-LU-10 antigen expression by such tissues. The NR-LU-10 antigen has been further described by Varki et al., "Antigens Associated with a Human Lung Adenocarcinoma Defined by Monoclonal Antibodies," *Cancer Research*, 44: 681–687, 1984, and Okabe et al., "Monoclonal Antibodies to Surface Antigens of Small Cell Carcinoma of the Lung," *Cancer Research*, 44: 5273–5278, 1984.

The tissue specimens were scored in accordance with three reactivity parameters: (1) the intensity of the reaction; (2) the uniformity of the reaction within the cell type; and (3) the percentage of cells reactive with the antibody. These three values are combined into a single weighted comparative value between 0 and 500, with 500 being the most intense reactivity. This comparative value facilitates comparison of different tissues. Table B includes a summary reactivity value, the number of tissue samples examined and the number of samples that reacted positively with NR-LU-10.

Methods for preparing antibodies that bind to epitopes of the NR-LU-10 antigen are described in U.S. Pat. No. 5,084,396. Briefly, such antibodies may be prepared by the following procedure:

absorbing a first monoclonal antibody directed against a first epitope of a polyvalent antigen onto an inert, insoluble matrix capable of binding immunoglobulin, thereby forming an immunosorbent;

combining the immunosorbent with an extract containing polyvalent NR-LU-10 antigen, forming an insolubilized immune complex wherein the first epitope is masked by the first monoclonal antibody;

TABLE A

TUMOR REACTIVITY OF ANTIBODY

| Organ/Cell Type Tumor | #Pos/ Exam | Intensity[a] Avg. | Range | Percent[b] Avg. | Range | Uniformity[c] Avg. | Range |
|---|---|---|---|---|---|---|---|
| Pancreas Carcinoma | 6/6 | 3 | 3 | 100 | 100 | 2.3 | 2–3 |
| Prostate Carcinoma | 9/9 | 2.8 | 2–3 | 95 | 80–100 | 2 | 1–3 |
| Lung Adenocarcinoma | 8/8 | 3 | 3 | 100 | 100 | 2.2 | 1–3 |
| Lung Small Cell Carcinoma | 2/2 | 3 | 3 | 100 | 100 | 2 | 2 |
| Lung Squamous Cell Carcinoma | 8/8 | 2.3 | 2–3 | 73 | 5–100 | 1.8 | 1–3 |
| Renal Carcinoma | 8/9 | 2.2 | 2–3 | 83 | 75–100 | 1 | 1 |
| Breast Adenocarcinoma | 23/23 | 2.9 | 2–3 | 97 | 75–100 | 2.8 | 1–3 |
| Colon Carcinoma | 12/12 | 2.9 | 2–3 | 98 | 95–100 | 2.9 | 2–3 |
| Malignant Melanoma Ocular | 0/2 | 0 | 0 | 0 | 0 | 0 | 0 |
| Malignant Melanoma | 0/11 | 0 | 0 | 0 | 0 | 0 | 0 |
| Ovarian Carcinoma | 35/35 | 2.9 | 2–3 | 200 | 100 | 2.2 | 1–3 |
| Undifferentiated Carcinoma | 1/1 | 2 | 2 | 90 | 90 | 2 | 2 |
| Osteasarcoma | 1/1 | 2 | 2 | 20 | 20 | 1 | 1 |
| Synovial Sarcoma | 0/1 | 0 | 0 | 0 | 0 | 0 | 0 |
| Lymphoma | 0/2 | 0 | 0 | 0 | 0 | 0 | 0 |
| Liposarcoma | 0/2 | 0 | 0 | 0 | 0 | 0 | 0 |
| Uterine Leiomyosarcoma | 0/1 | 0 | 0 | 0 | 0 | 0 | 0 |

[a]Rated from 0–3, with 3 representing highest intensity
[b]Percentage of cells stained within the examined tissue section.
[c]Rates from 0–3, with 3 representing highest uniformity.

TABLE B

| Organ/Cell Type | # Pos/Exam | Summary Reactivity |
|---|---|---|
| Adenoid | | |
| Epithelium | 3/3 | 433 |
| Lymphoid Follicle-Central | 0/3 | 0 |
| Lymphoid Follicle-Peripheral | 0/3 | 0 |
| Mucus Gland | 2/2 | 400 |
| Adipose Tissue | | |
| Fat Cells | 0/3 | 0 |
| Adrenal | | |
| Zona Fasciculata Cortex | 0/3 | 0 |
| Zona Glomerulosa Cortex | 0/3 | 0 |
| Zona Reticularis Cortex | 0/3 | 0 |
| Medulla | 0/3 | 0 |
| Aorta | | |
| Endothelium | 0/3 | 0 |
| Elastic Interna | 0/3 | 0 |
| Tunica Adventitia | 0/3 | 0 |
| Tunica Media | 0/3 | 0 |
| Brain-Cerebellum | | |
| Axons, Myelinated | 0/3 | 0 |
| Microglia | 0/3 | 0 |
| Neurons | 0/3 | 0 |
| Purkenje's Cells | 0/3 | 0 |

TABLE B-continued

| Organ/Cell Type | # Pos/Exam | Summary Reactivity |
|---|---|---|
| Brain-Cerebrum | | |
| Axons, Myelinated | 0/3 | 0 |
| Microglia | 0/3 | 0 |
| Neurons | 0/3 | 0 |
| Brain-Midbrain | | |
| Axons, Myelinated | 0/3 | 0 |
| Microglia | 0/3 | 0 |
| Neurons | 0/3 | 0 |
| Colon | | |
| Mucosal Epithelium | 3/3 | 500 |
| Muscularis Externa | 0/3 | 0 |
| Muscularis Mucosa | 0/3 | 0 |
| Nerve Ganglia | 0/3 | 0 |
| Serosa | 0/1 | 0 |
| Duodenum | | |
| Mucosal Epithelium | 3/3 | 500 |
| Muscularis Mucosa | 0/3 | 0 |
| Epididymis | | |
| Epithelium | 3/3 | 419 |
| Smooth Muscle | 0/3 | 0 |
| Spermatozoa | 0/1 | 0 |
| Esophagus | | |
| Epithelium | 3/3 | 86 |
| Mucosal Gland | 2/2 | 450 |
| Smooth Muscle | 0/3 | 0 |
| Gall Bladder | | |
| Mucosal Epithelium | 0/3 | 467 |
| Smooth Muscle | 0/3 | 0 |
| Heart | | |
| Myocardium | 0/3 | 0 |
| Serosa | 0/1 | 0 |
| Ileum | | |
| Lymph Node | 0/2 | 0 |
| Mucosal Epithelium | 0/2 | 0 |
| Muscularis Externa | 0/1 | 0 |
| Muscularis Mucosa | 0/2 | 0 |
| Nerve Ganglia | 0/1 | 0 |
| Serosa | 0/1 | 0 |
| Jejunum | | |
| Lymph Node | 0/1 | 0 |
| Mucosal Epithelium | 2/2 | 400 |
| Muscularis Externa | 0/2 | 0 |
| Muscularis Mucosa | 0/2 | 0 |
| Nerve Ganglia | 0/2 | 0 |
| Serosa | 0/1 | 0 |
| Kidney | | |
| Collecting Tubules | 2/3 | 160 |
| Distal Convoluted Tubules | 3/3 | 500 |
| Glomerular Epithelium | 0/3 | 0 |
| Mesangial | 0/3 | 0 |
| Proximal Convoluted Tubules | 3/3 | 500 |
| Liver | | |
| Bile Duct | 3/3 | 500 |
| Central Lobular Hepatocyte | 1/3 | 4 |
| Periportal Hepatocyte | 1/3 | 40 |
| Kupffer Cells | 0/3 | 0 |
| Lung | | |
| Alveolar Macrophage | 0/3 | 0 |
| Bronchial Epithelium | 0/2 | 0 |
| Bronchial Smooth Muscle | 0/2 | 0 |
| Pneumocyte Type I | 3/3 | 354 |
| Pneumocyte Type II | 3/3 | 387 |

TABLE B-continued

| Organ/Cell Type | # Pos/Exam | Summary Reactivity |
|---|---|---|
| Lymph Node | | |
| Lymphoid Follicle-Central | 0/3 | 0 |
| Lymphoid Follicle-Peripheral | 0/3 | 0 |
| Mammary Gland | | |
| Aveolar Epithelium | 3/3 | 500 |
| Duct Epithelium | 3/3 | 500 |
| Myoepithelium | 0/3 | 0 |
| Muscle Skeletal | | |
| Muscle Fiber | 0/3 | 0 |
| Nerve | | |
| Axon, Myelinated | 0/2 | 0 |
| Endoneurium | 0/2 | 0 |
| Neurolemma | 0/2 | 0 |
| Neuron | 0/2 | 0 |
| Perineurium | 0/2 | 0 |
| Ovary | | |
| Corpus Luteum | 0/3 | 0 |
| Epithelium | 1/1 | 270 |
| Granulosa | 1/3 | 400 |
| Serosa | 0/3 | 0 |
| Theca | 0/3 | 0 |
| Oviduct | | |
| Epithelium | 1/1 | 500 |
| Smooth Muscle | 0/3 | 0 |
| Pancreas | | |
| Acinar Cell | 3/3 | 500 |
| Duct Epithelium | 3/3 | 500 |
| Islet Cell | 3/3 | 500 |
| Peritoneum | | |
| Mesothelium | 0/1 | 0 |
| Pituitary | | |
| Adenohypophysis | 2/2 | 500 |
| Neurohypophysis | 0/2 | 0 |
| Placenta | | |
| Trophoblasts | 0/3 | 0 |
| Prostate | | |
| Concretions | 0/3 | 0 |
| Glandular Epithelium | 3/3 | 400 |
| Smooth Muscle | 0/3 | 0 |
| Rectum | | |
| Lymph Node | 0/2 | 0 |
| Mucosal Epithelium | 0/2 | 0 |
| Muscularis Externa | 0/1 | 0 |
| Muscularis Mucosa | 0/3 | 0 |
| Nerve Ganglia | 0/3 | 0 |
| Salivary Gland | | |
| Acinar Epithelium | 3/3 | 500 |
| Duct Epithelium | 3/3 | 500 |
| Skin | | |
| Apocrine Glands | 3/3 | 280 |
| Basal Layer | 3/3 | 33 |
| Epithelium | 1/3 | 10 |
| Follicle | 1/1 | 190 |
| Stratum Corneum | 0/3 | 0 |
| Spinal Cord | | |
| Axons, Myelinated | 0/2 | 0 |
| Microglial | 0/2 | 0 |
| Neurons | 0/2 | 0 |
| Spleen | | |
| Lymphoid Follicle-Central | 0/3 | 0 |

TABLE B-continued

| Organ/Cell Type | # Pos/Exam | Summary Reactivity |
|---|---|---|
| Lymphoid Follicle-Peripheral | 0/3 | 0 |
| Trabecular Smooth Muscle | 0/3 | 0 |
| Stomach | | |
| Chief Cells | 3/3 | 290 |
| Mucosal Epithelium | 3/3 | 367 |
| Muscularis Mucosa/Externa | 0/3 | 0 |
| Parietal Cells | 3/3 | 290 |
| Smooth Muscle | 0/3 | 0 |
| Stromal Tissue | | |
| Adipose | 0/63 | 0 |
| Arteriolar Smooth Muscle | 0/120 | 0 |
| Endothelium | 0/120 | 0 |
| Fibrous Connective Tissue | 0/120 | 0 |
| Macrophages | 0/117 | 0 |
| Mast Cells/Eosinophils | 0/86 | 0 |
| Testis | | |
| Interstitial Cells | 0/3 | 0 |
| Sertoli Cells | 3/3 | 93 |
| Thymus | | |
| Hassal's Epithelium | 3/3 | 147 |
| Hassal's Keratin | 3/3 | 333 |
| Lymphoid Cortex | 0/3 | 0 |
| Lymphoid Medulla | 3/3 | 167 |
| Thyroid | | |
| C-cells | 0/3 | 0 |
| Colloid | 0/3 | 0 |
| Follicular Epithelium | 3/3 | 500 |
| Tonsil | | |
| Epithelium | 1/3 | 500 |
| Lymphoid Follicle-Central | 0/3 | 0 |
| Lymphoid Follicle-Peripheral | 0/3 | 0 |
| Mucus Gland | 1/1 | 300 |
| Striated Muscle | 0/3 | 0 |
| Umbilical cord | | |
| Epithelium | 0/3 | 0 |
| Urinary Bladder | | |
| Mucosal Epithelium | 3/3 | 433 |
| Serosa | 0/1 | 0 |
| Smooth Muscle | 0/3 | 0 |
| Uterus | | |
| Endometrial Epithelium | 3/3 | 500 |
| Endometrial Glands | 3/3 | 500 |
| Smooth Muscle | 0/3 | 0 |
| Vagina/Cervix | | |
| Epithelial Glands | 1/1 | 500 |
| Smooth Muscle | 0/2 | 0 |
| Squamous Epithelium | 1/1 | 200 | immunizing an animal with the insolubilized immune complex;

fusing spleen cells from the immunized animal to myeloma cells to form a hybridoma capable of producing a second monoclonal antibody directed against a second epitope of the polyvalent antigen;

culturing the hybridoma to produce the second monoclonal antibody; and collecting the second monoclonal antibody as a product of the hybridoma.

Consequently, monoclonal antibodies NR-LU-01, NR-LU-02 and NR-LU-03, prepared in accordance with the procedures described in the aforementioned patent, are exemplary targeting moieties useful in this aspect of the present invention.

Additional antibodies reactive with the NR-LU-10 antigen may also be prepared by standard hybridoma production and screening techniques. Any hybridoma clones so produced and identified may be further screened as described above to verify antigen and tissue reactivity.

The invention is further described through presentation of the following examples. These examples are offered by way of illustration, and not by way of limitation.

EXAMPLE I

Synthesis of a Chelate-Biotin Conjugate

A chelating compound that contains an $N_3S$ chelating core was attached via an amide linkage to biotin. Radiometal labeling of an exemplary chelate-biotin conjugate is illustrated below.

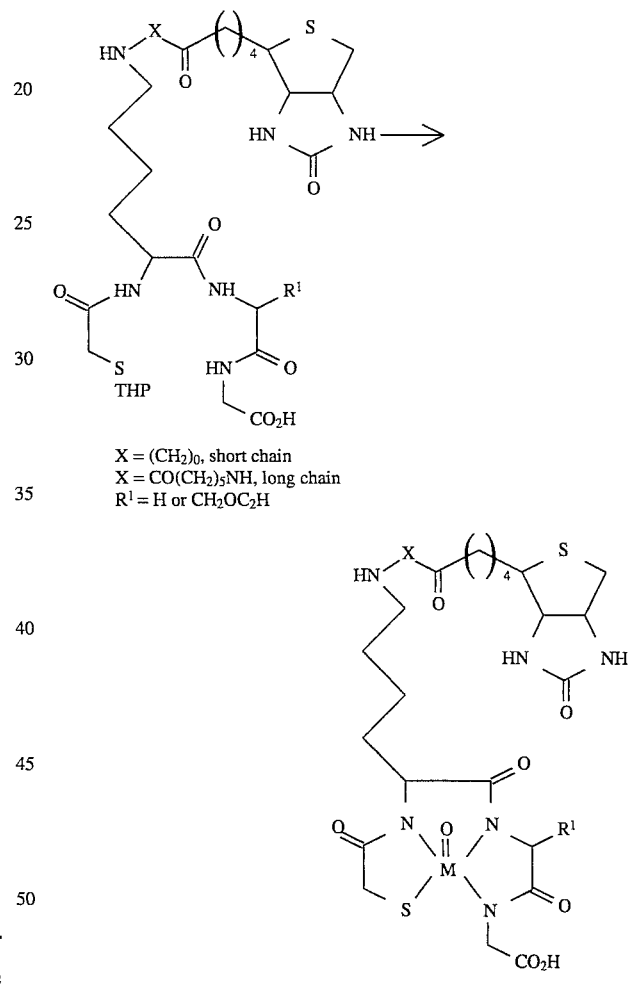

$X = (CH_2)_0$, short chain
$X = CO(CH_2)_5NH$, long chain
$R^1 = H$ or $CH_2OC_2H$ M = Tc or Rc The spacer group "X" permits the biotin portion of the conjugate to be sterically available for avidin binding. When "$R^1$" is a carboxylic acid substituent (for instance, $CH_2COOH$), the conjugate exhibits improved water solubility, and further directs in vivo excretion of the radiolabeled biotin conjugate toward renal rather than hepatobiliary clearance.

Briefly, N-α-Cbz-N-Σ-t-BOC protected lysine was converted to the succinimidyl ester with NHS and DCC, and then condensed with aspartic acid β-t-butyl ester. The resultant dipeptide was activated with NHS and DCC, and then condensed With glycine t-butyl ester. The Cbz group was removed by hydrogenolysis, and the amine was acylated using tetrahydropyranyl mercaptoacetic acid succinimidyl ester, yielding S-(tetrahydropyranyl)-mercaptoacetyl-lysine. Trifluoroacetic acid cleavage of the N-t-BOC group and t-butyl esters, followed by condensation with LC-biotin-NHS ester provided (Σ-caproylamide biotin)aspartyl glycine. This synthetic method is illustrated below.

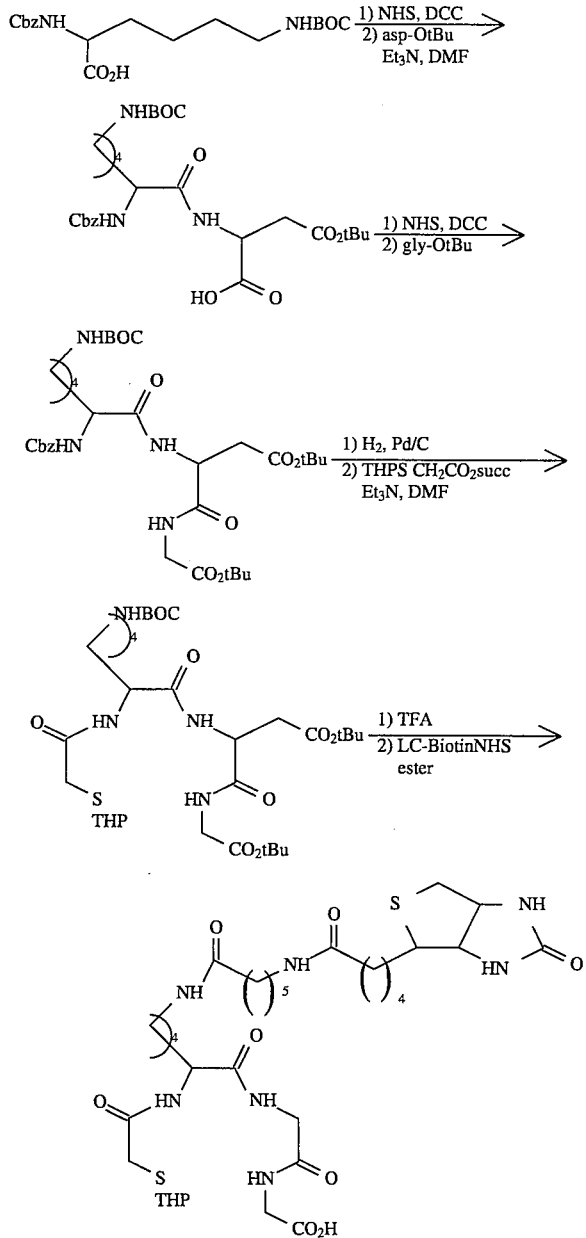

$^1$H NMR: (CD$_3$OD, 200 MHz Varian): 1.25–1.95 (m, 24H), 2.15–2.25 (broad t, 4H), 2.65–3.05 (m, 4H), 3.30–3.45 (dd, 2H), 3.50–3.65 (ddd, 2H), 3.95 (broad s, 2H), 4.00–4.15 (m, 1H), 4.25–4.35 (m, 1H), 4.45–4.55 (m, 1H), 4.7–5.05 (m overlapping with HOD).

Elemental Analysis: C, H, N for C$_{35}$H$_{57}$N$_7$O$_{11}$S$_2$·H$_2$O; calculated: 50.41, 7.13, 11.76; found: 50.13, 7.14, 11.40.

EXAMPLE II

Preparation of a Technetium or Rhenium Radiolabeled Chelate-Biotin Conjugate

The chelate-biotin conjugate of Example I was radiolabeled with either $^{99m}$Tc pertechnetate or $^{186}$Re perrhenate. Briefly, $^{99m}$Tc pertechnetate was reduced with stannous chloride in the presence of sodium gluconate to form an intermediate Tc-gluconate complex. The chelate-biotin conjugate of Example I was added and heated to 100° C. for 10 min at a pH of about 1.8 to about 3.3. The solution was neutralized to a pH of about 6 to about 8, and yielded an N$_3$S-coordinated $^{99m}$Tc-chelate-biotin conjugate. C-18 HPLC gradient elution using 5–60% acetonitrile in 1% acetic acid demonstrated two anomers at 97% or greater radiochemical yield using δ detection.

Alternatively, $^{186}$Re perrhenate was spiked with cold ammonium perrhenate, reduced with stannous chloride, and complexed with citrate. The chelate-biotin conjugate of Example I was added and heated to 90° C. for 30 min at a pH of about 2 to 3. The solution was neutralized to a pH of about 6 to about 8, and yielded an N$_3$S-coordinated $^{186}$Re-chelate-biotin conjugate. C-18 HPLC gradient elution using 5–60% acetonitrile in 1% acetic acid resulted in radiochemical yields of 85–90%. Subsequent purification over a C-18 reverse phase hydrophobic column yielded material of 99% purity.

EXAMPLE III

In Vitro Analysis of Radiolabeled Chelate-Biotin Conjugates

Both the $^{99m}$Tc- and $^{186}$Re-chelate-biotin conjugates were evaluated in vitro. When combined with excess avidin (about 100-fold molar excess), 100% of both radiolabeled biotin conjugates complexed with avidin.

A $^{99m}$Tc-biotin conjugate was subjected to various chemical challenge conditions. Briefly, $^{99m}$Tc-chelate-biotin conjugates were combined with avidin and passed over a 5 cm size exclusion gel filtration column. The radiolabeled biotin-avidin complexes were subjected to various chemical challenges (see Table 1), and the incubation mixtures were centrifuged through a size exclusion filter. The percent of radioactivity retained (indicating avidin-biotin-associated radiolabel) is presented in Table 1. Thus, upon chemical challenge, the radiometal remained associated with the macromolecular complex.

TABLE 1

| Chemical Challenge of $^{99m}$Tc-Chelate-Biotin-Avidin Complexes | | | |
|---|---|---|---|
| Challenge | | % Radioactivity Retained | |
| Medium | pH | 1 h, 37° C. | 18 h, RT |
| PBS | 7.2 | 99 | 99 |
| Phosphate | 8.0 | 97 | 97 |
| 10 mM cysteine | 8.0 | 92 | 95 |
| 10 mM DTPA | 8.0 | 99 | 98 |
| 0.2 M carbonate | 10.0 | 97 | 94 |

In addition, each radiolabeled biotin conjugate was incubated at about 50 μg/ml with serum; upon completion of the incubation, the samples were subjected to instant thin layer chromatography (ITLC) in 80% methanol. Only 2–4% of the radioactivity remained at the origin (i.e., associated with protein); this percentage was unaffected by the addition of exogenous biotin. When the samples were analyzed using size exclusion H-12 FPLC with 0.2M phosphate as mobile phase, no association of radioactivity with serum macromolecules was observed.

Each radiolabeled biotin conjugate was further examined using a competitive biotin binding assay. Briefly, solutions containing varying ratios of D-biotin to radiolabeled biotin conjugate were combined with limiting avidin at a constant total biotin:avidin radio. Avidin binding of each radiolabeled biotin conjugate was determined by ITLC, and was compared to the theoretical maximum stoichiometric binding (as determined by the HABA spectrophotometric assay of Green, *Biochem. J.* 94:23c–24c, 1965). No significant difference in avidin binding was observed between each radiolabeled biotin conjugate and D-biotin.

EXAMPLE IV

In Vivo Analysis of Radiolabeled Chelate-Biotin Conjugates Administered After Antibody Pretargeting The $^{186}$Re-chelate-biotin conjugate of Example I was studied in an animal model of a three-step antibody pretargeting protocol. Generally, this protocol involved: (i) prelocalization of biotinylated monoclonal antibody; (ii) administration of avidin for formation of a "sandwich" at the target site and for clearance of residual circulating biotinylated antibody; and (iii) administration of the 186Re-biotin conjugate for target site localization and rapid blood clearance.

A. Preparation and Characterization of Biotinylated Antibody

Biotinylated NR-LU-10 was prepared according to either of the following procedures. The first procedure involved derivatization of antibody via lysine ε-amino groups. NR-LU-10 was radioiodinated at tyrosines using chloramine T and either $^{125}$I or $^{131}$I sodium iodide. The radioiodinated antibody (5–10 mg/ml) was then biotinylated using biotinamido caproate NHS ester in carbonate buffer, pH 8.5, containing 5% DMSO, according to the scheme below.

TABLE 2

Effect of Lysine Biotinylation on Immunoreactivity

| Molar Offering (Biotins/Ab) | Measured Derivitization (Biotins/Ab) | Immunoassessment (%) | |
|---|---|---|---|
| | | ELISA | Cell Binding |
| 5:1 | 3.4 | 86 | |
| 10:1 | 8.5 | 73 | 100 |
| 13:1 | 11.1 | 69 | 102 |
| 20:1 | 13.4 | 36 | 106 |
| 40:1 | 23.1 | 27 | |

Alternatively, NR-LU-10 was biotinylated using thiol groups generated by reduction of cystines. Derivitization of thiol groups was hypothesized to be less compromising to antibody immunoreactivity. NR-LU-10 was radioiodinated using p-aryltin phenylate NHS ester (PIP-NHS) and either $^{125}$I or $^{131}$I sodium iodide. Radioiodinated NR-LU-10 was incubated with 25 mM dithiothreitol and purified using size exclusion chromatography. The reduced antibody (containing free thiol groups) was then reacted with a 10- to 100-fold molar excess of N-iodoacetyl-n'-biotinyl hexylene diamine in phosphate-buffered saline (PBS), pH 7.5, containing 5% DMSO (v/v).

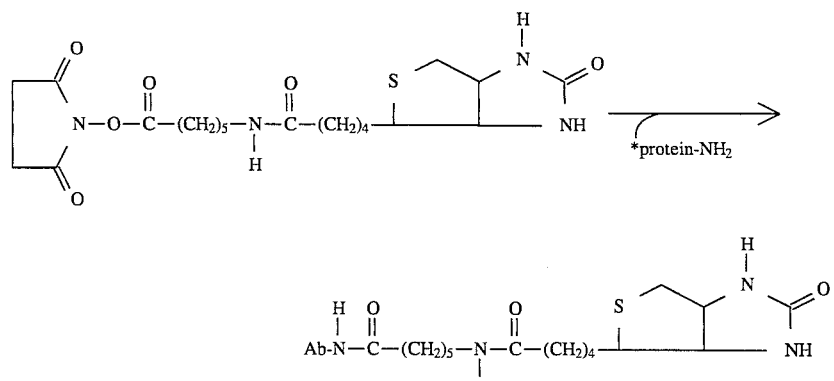

The impact of lysine biotinylation on antibody immunoreactivity was examined. As the molar offering of biotin:antibody increased from 5:1 to 40:1, biotin incorporation increased as expected (measured using the HABA assay and pronase-digested product) (Table 2, below). Percent of biotinylated antibody immunoreactivity as compared to native antibody was assessed in a limiting antigen ELISA assay. The immunoreactivity percentage dropped below 70% at a measured derivitization of 11.1:1; however, at this level of derivitization, no decrease in antigen-positive cell binding (performed with LS-180 tumor cells at antigen excess). Subsequent experiments used antibody derivitized at a biotin:antibody ratio of 10:1.

TABLE 3

Effect of Thiol Biotinylation on Immunoreactivity

| Molar Offering (Biotins/Ab) | Measured Derivitization (Biotins/Ab) | Immunoassessment (%) | |
|---|---|---|---|
| | | ELISA | Cell Binding |
| 10:1 | 4.7 | 114 | |
| 50:1 | 6.5 | 102 | 100 |
| 100:1 | 6.1 | 95 | 100 |

As shown in Table 3, at a 50:1 or greater biotin:antibody molar offering, only 6 biotins per antibody were incorporated. No significant impact on immunoreactivity was observed.

The lysine- and thiol-derivitized biotinylated antibodies ("antibody (lysine)" and "antibody (thiol)", respectively) were compared. Molecular sizing on size exclusion FPLC demonstrated that both biotinylation protocols yielded monomolecular IgGs. Biotinylated antibody (lysine) had an apparent molecular weight of 160 kD, while biotinylated antibody (thiol) had an apparent molecular weight of 180 kD. Reduction of endogenous sulfhydryls (i.e., disulfides) to thiol groups, followed by conjugation with biotin, may produce a somewhat unfolded macromolecule. If so, the antibody (thiol) may display a larger hydrodynamic radius and exhibit an apparent increase in molecular weight by chromatographic analysis. Both biotinylated antibody species exhibited 98% specific binding to immobilized avidin-agarose.

Further comparison of the biotinylated antibody species was performed using non-reducing SDS-PAGE, using a 4% stacking gel and a 5% resolving gel. Biotinylated samples were either radiolabeled or unlabeled and were combined with either radiolabeled or unlabeled avidin or streptavidin. Samples were not boiled prior to SDS-PAGE analysis. The native antibody and biotinylated antibody (lysine) showed similar migrations; the biotinylated antibody (thiol) produced two species in the 50–75 kD range. These species may represent two thiol-capped species. Under these SDS-PAGE conditions, radiolabeled streptavidin migrates as a 60 kD tetramer. When 400 μg/ml radiolabeled streptavidin was combined with 50 μg/ml biotinylated antibody (analogous to "sandwiching" conditions in vivo), both antibody species formed large molecular weight complexes. However, only the biotinylated antibody (thiol)-streptavidin complex moved from the stacking gel into the resolving gel, indicating a decreased molecular weight as compared to the biotinylated antibody ( lysine ) -streptavidin complex.

B. Blood Clearance of Biotinylated Antibody Species

Radioiodinated biotinylated NR-LU-10 (lysine or thiol) was intravenously administered to non-tumored nude mice at a dose of 100 μg. At 24 h post-administration of radioiodinated biotinylated NR-LU-10, mice were intravenously injected with either saline or 400 μg of avidin. With saline administration, blood clearances for both biotinylated antibody species were biphasic and similar to the clearance of native NR-LU-10 antibody.

In the animals that received avidin intravenously at 24 h, the biotinylated antibody (lysine) was cleared (to a level of 5% of injected dose) within 15 min of avidin administration (avidin:biotin=10:1). With the biotinylated antibody (thiol), avidin administration (10:1 or 25:1) reduced the circulating antibody level to about 35% of injected dose after two hours. Residual radiolabeled antibody activity in the circulation after avidin administration was examined in vitro using immobilized biotin. This analysis revealed that 85% of the biotinylated antibody was complexed with avidin. These data suggest that the biotinylated antibody (thiol)-avidin complexes that were formed were insufficiently crosslinked to be cleared by the RES.

Blood clearance and biodistribution studies of biotinylated antibody (lysine) 2 h post-avidin or post-saline administration were performed. Avidin administration significantly reduced the level of biotinylated antibody in the blood (see FIG. 1), and increased the level of biotinylated antibody in the liver and spleen. Kidney levels of biotinylated antibody were similar.

EXAMPLE V

In Vivo Characterization of $^{186}$Re-Chelate-Biotin Conjugates in a Three-Step Pretargeting Protocol A $^{186}$Re-chelate-biotin conjugate of Example I (MW≈1000; specific activity=1–2 mCi/mg) was examined in a three-step pretargeting protocol in an animal model. More specifically, 18–22 g female nude mice were implanted subcutaneously with LS-180 human colon tumor xenografts, yielding 100–200 mg tumors within 10 days of implantation.

NR-LU-10 antibody (MW≈150 kD) was radiolabeled with $^{125}$I/Chloramine T and biotinylated via lysine residues (as described in Example VI.A, above). Avidin (MW≈66 kD) was radiolabeled with $^{131}$I/PIP-NHS (as described for radioiodination of NR-LU-10 in Example IV.A., above). The experimental protocol was as follows:

| Group 1: | Time 0, inject 100 μg $^{125}$I-labeled, biotinylated NR-LU-10 |
| | Time 24 h, inject 400 μg $^{131}$I-labeled avidin |
| | Time 26 h, inject 60 μg $^{186}$Re-chelate-biotin conjugate |
| Group 2: (control) | Time 0, inject 400 μg $^{131}$I-labeled avidin |
| | Time 2 h, inject 60 μg $^{186}$Re-chelate-biotin conjugate |
| Group 3: (control) | Time 0, inject 60 μg $^{186}$Re-chelate-biotin conjugate |

The three radiolabels employed in this protocol are capable of detection in the presence of each other. It is also noteworthy that the sizes of the three elements involved are logarithmically different—antibody≡150,000; avidin≡66,000; and biotin≡1,000. Biodistribution analyses were performed at 2, 6, 24, 72 and 120 h after administration of the $^{186}$Re-chelate-biotin conjugate.

Certain preliminary studies were performed in the animal model prior to analyzing the $^{186}$Re-chelate-biotin conjugate in a three-step pretargeting protocol. First, the effect of biotinylated antibody on blood clearance of avidin was examined. These experiments showed that the rate and extent of avidin clearance was similar in the presence or absence of biotinylated antibody. Second, the effect of biotinylated antibody and avidin on blood clearance of the $^{186}$Re-chelate-biotin conjugate was examined; blood clearance was similar in the presence or absence of biotinylated antibody and avidin.

Third, tumor uptake of biotinylated antibody administered at time 0 or of avidin administered at time 24 h was examined. At 25 h, about 350 pmol/g biotinylated antibody was present at the tumor; at 32 h the level was about 300 pmol/g; at 48 h, about 200 pmol/g; and at 120 h, about 100 pmol/g. Avidin uptake at the same time points was about 250, 150, 50 and 0 pmol/g, respectively. From the same experiment, tumor to blood ratios were determined for biotinylated antibody and for avidin. From 32 h to 120 h, the ratios of tumor to blood were very similar.

The three-step pretargeting protocol (described for Group 1, above) was then examined. More specifically, tumor uptake of the $^{186}$Re-chelate-biotin conjugate in the presence or absence of biotinylated antibody and avidin was determined. In the absence of biotinylated antibody and avidin, the $^{186}$Re-chelate-biotin conjugate displayed a slight peak 2 h post-injection, which was substantially cleared from the tumor by about 5 h. In contrast, at 2 h post-injection in the presence of biotinylated antibody and avidin (specific), the $^{186}$Re-chelate-biotin conjugate reached a peak in tumor approximately 7 times greater than that observed in the absence of biotinylated antibody and avidin. Further, the specifically bound $^{186}$Re-chelate-biotin conjugate was retained at the tumor at significant levels for more than 50 h. Tumor to blood ratios determined in the same experiment increased significantly over time (i.e., T:B≈8 at 30 h; ≈15 at 100 h; ≈35 at 140 h).

Tumor uptake of the [186]Re-chelate-biotin conjugate has further been shown to be dependent on the dose of biotinylated antibody administered. At 0 μg of biotinylated antibody, about 200 pmol/g of [186]Re-chelate-biotin conjugate was present at the tumor at 2 h after administration; at 50 μg antibody, about 500 pmol/g of [186]Re-chelate-biotin conjugate; and at 100 μg antibody, about 1,300 pmol/g of [186]Re-chelate-biotin conjugate.

Figure 2:
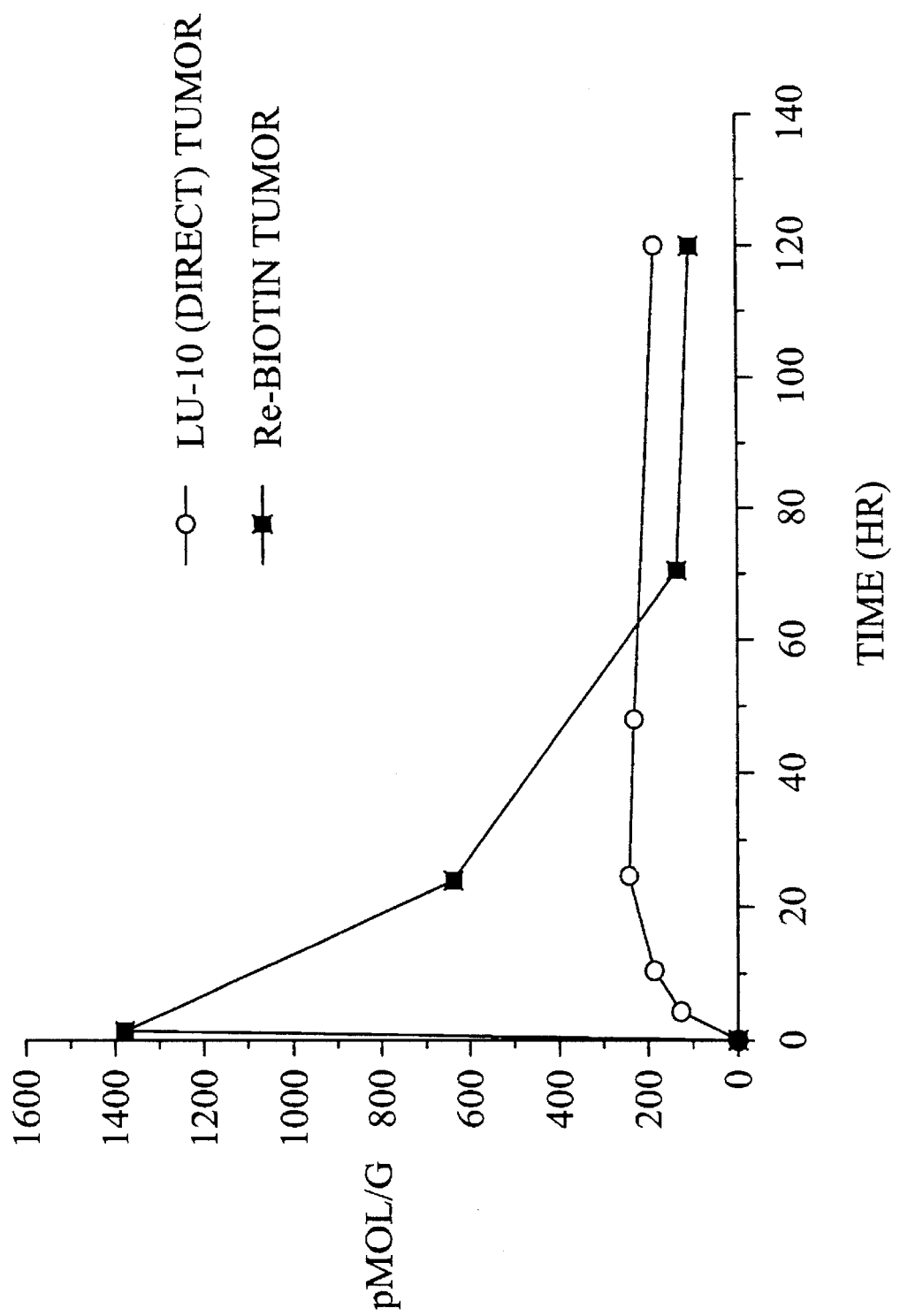
FIG. 2 depicts radiorhenium tumor uptake in a three-step pretargeting protocol, as compared to administration of radiolabeled antibody (conventional means involving antibody that is covalently linked to chelated radiorhenium).

Rhenium tumor uptake via the three-step pretargeting protocol was compared to tumor uptake of the same antibody radiolabeled through chelate covalently attached to the antibody (conventional procedure). The results of this comparison are depicted in FIG. 2. Blood clearance and tumor uptake were compared for the chelate directly labeled rhenium antibody conjugate and for the three-step pretargeted sandwich. Areas under the curves (AUC) and the ratio of $AUC_{tumor}/AUC_{blood}$ were determined. For the chelate directly labeled rhenium antibody conjugate, the ratio of $AUC_{tumor}/AUC_{blood}=24055/10235$; for the three-step pretargeted sandwich, the ratio of $AUC_{tumor}/AUC_{blood}=46764/6555$.

EXAMPLE VI

Preparation of Chelate-Biotin Conjugates Having Improved Biodistribution Properties The biodistribution of $^{111}$In-labeled-biotin derivatives varies greatly with structural changes in the chelate and the conjugating group. Similar structural changes may affect the biodistribution of technetium- and rhenium-biotin conjugates. Accordingly, methods for preparing technetium- and rhenium-biotin conjugates having optimal clearance from normal tissue are advantageous.

A. Neutral MAMA Chelate/Conjugate

A neutral MAMA chelate-biotin conjugate is prepared according to the following scheme.

a) MAMA ligand

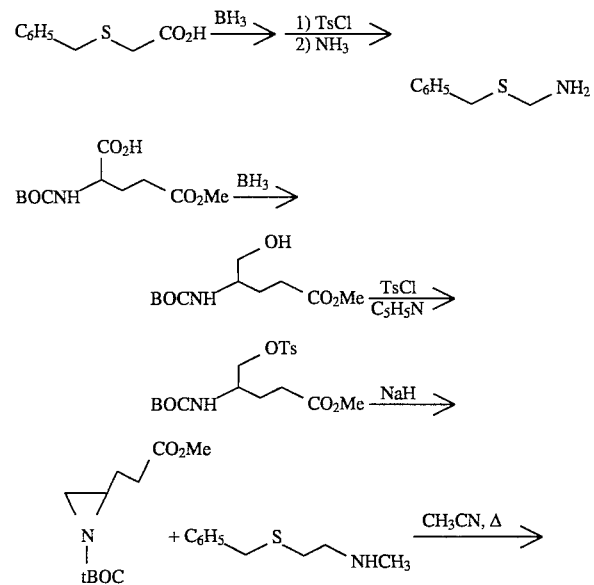

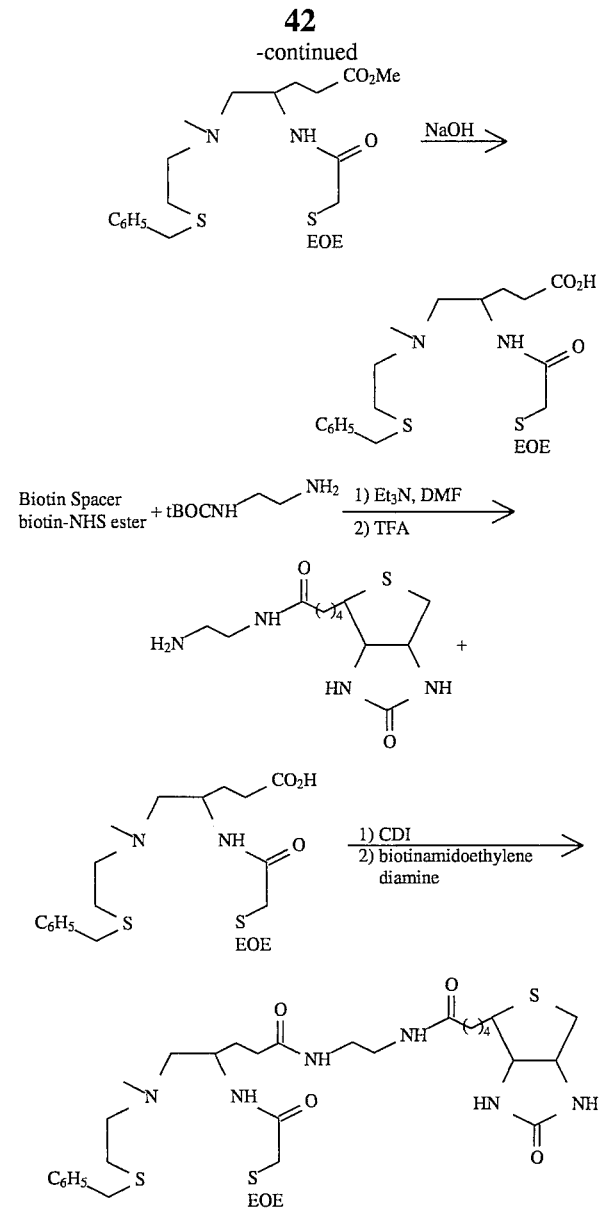

The resultant chelate-biotin conjugate shows superior kidney excretion. Although the net overall charge of the conjugate is neutral, the polycarboxylate nature of the molecule generates regions of hydrophilicity and hydrophobicity. By altering the number and nature of the carboxylate groups within the conjugate, excretion may be shifted from kidney to gastrointestinal routes. For instance, neutral compounds are cleared by the kidneys; anionic compounds are cleared through the GI system.

B. Polylysine Derivitization

Conjugates containing polylysine may also exhibit beneficial biodistribution properties. With whole antibodies, derivitization with polylysine may skew the biodistribution of conjugate toward liver uptake. In contrast, derivitization of Fab fragments with polylysine results in low levels of both liver and kidney uptake; blood clearance of these conjugates is similar to that of Fab covalently linked to chelate. An exemplary polylysine derivitized chelate-biotin conjugate is illustrated below.

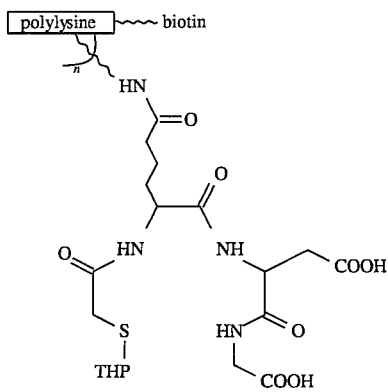

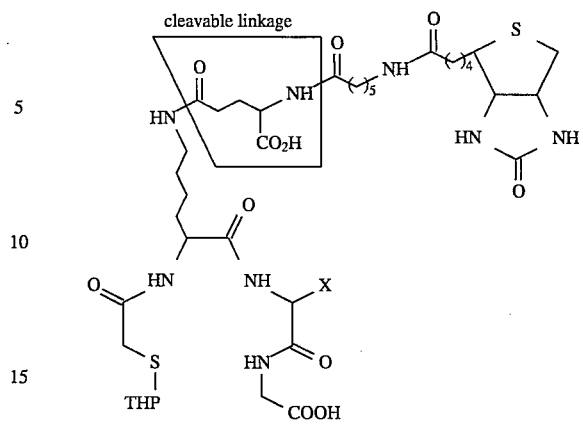

X = H$_2$ or CH$_2$CO$_2$H

D. Serine Linker With O-Polar Substituent

Sugar substitution of N$_3$S chelates renders such chelates water soluble. Sulfonates, which are fully ionized at physiological pH, improve water solubility of the chelate-biotin conjugate depicted below.

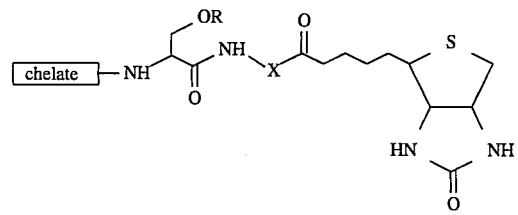

R = a sugar such as ribose or glucose or SO$_2$OH
X = (CH$_2$)$_0$ or CO(CH$_2$)$_4$ This compound is synthesized according to the standard reaction procedures. Briefly, biocytin is condensed with N-t-BOC-(O-sulfonate or O-glucose) serine NHS ester to give N-t-BOC-(O-sulfonate or O-glucose) serine biocytinamide. Subsequent cleavage of the N-t-BOC group with TFA and condensation with ligand NHS ester in DMF with triethylamine provides ligand-amidoserine(O-sulfonate or O-glucose)biocytinamide.

EXAMPLE VII

Preparation and Characterization of PIP-Radioiodinated Biotin

Radioiodinated biotin derivatives prepared by exposure of poly-L-lysine to excess NHS-LC-biotin and then to Bolton-Hunter N-hydroxysuccinimide esters in DMSO has been reported. After purification, this product was radiolabeled by the iodogen method (see, for instance, Del Rosario et al., *J. Nucl. Med.* 32:5, 1991, 993 (abstr.)). Because of the high molecular weight of the resultant radioiodinated biotin derivative, only limited characterization of product (i.e., radio-HPLC and binding to immobilized streptavidin) was possible.

Preparation of radioiodonated biotin according to the present invention provides certain advantages. First, the radioiodobiotin derivative is a low molecular weight compound that is amenable to complete chemical characterization. Second, the disclosed methods for preparation involve a single step and eliminate the need for a purification step.

Inclusion of polylysine in radiometal-chelate-biotin conjugates is therefore useful for minimizing or eliminating RES sequestration while maintaining good liver and kidney clearance of the conjugate. Polylysine derivatives offer the further advantages of: (1) increasing the specific activity of the radiometal-chelate-biotin conjugate; (2) permitting control of rate and route of blood clearance by varying the molecular weight of the polylysine polymer; and (3) increasing the circulation half-life of the conjugate for optimal tumor interaction.

Polylysine derivitization is accomplished by standard methodologies. Briefly, poly-L-lysine is acylated according to standard amino group acylation procedures (aqueous bicarbonate buffer, pH 8, added biotin-NHS ester, followed by chelate NHS ester). Alternative methodology involves anhydrous conditions using nitrophenyl esters in DMSO and triethyl amine. The resultant conjugates are characterized by UV and NMR specta.

The number of biotins attached to polylysine is determined by the HABA assay. Spectrophotometric titration is used to assess the extent of amino group derivitization. The radiometal-chelate-biotin conjugate is characterized by size exclusion.

C. Cleavable Linkage

Through insertion of a cleavable linker between the chelate and biotin portion of a radiometal-chelate-biotin conjugate, retention of the conjugate at the tumor relative to normal tissue may be enhanced. More specifically, linkers that are cleaved by enzymes present in normal tissue but deficient or absent in tumor tissue can increase tumor retention. As an example, the kidney has high levels of γ-glutamyl transferase; other normal tissues exhibit in vivo cleavage of γ-glutamyl prodrugs. In contrast, tumors are generally deficient in enzyme peptidases. The glutamyl-linked biotin conjugate depicted below is cleaved in normal tissue and retained in the tumor.

Briefly, iodobenzamide derivatives corresponding to biocytin (R=COOH) and biotinamidopentylamine (R=H) were prepared according to the following scheme. In this scheme, "X" may be any radiohalogen, including $^{125}$I, $^{131}$I, $^{123}$I, $^{211}$At and the like.

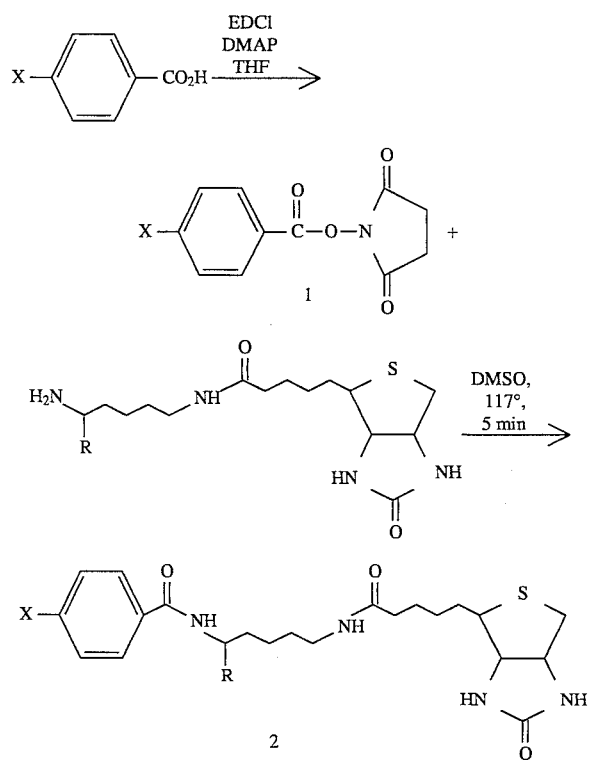

Preparation of 1 was generally according to Wilbur et al., *J. Nucl. Med.* 30:216–26, 1989, using a tributyltin intermediate. Water soluble carbodiimide was used in the above-depicted reaction, since the NHS ester 1 formed intractable mixtures with DCU. The NHS ester was not compatible with chromatography; it was insoluble in organic and aqueous solvents and did not react with biocytin in DMF or in buffered aqueous acetonitrile. The reaction between 1 and biocytin or 5-(biotinamido) pentylamine was sensitive to base. When the reaction of 1 and biocytin or the pentylamine was performed in the presence of triethylamine in hot DMSO, formation of more than one biotinylated product resulted. In contrast, the reaction was extremely clean and complete when a suspension of 1 and biocytin (4 mg/ml) or the pentylamine (4 mg/ml) was heated in DMSO at 117° C. for about 5 to about 10 min. The resultant $^{125}$I-biotin derivatives were obtained in 94% radiochemical yield. Optionally, the radioiodinated products may be purified using C-18 HPLC and a reverse phase hydrophobic column. Hereinafter, the resultant radioiodinated products 2 are referred to as PIP-biocytin (R=COOH) and PIP-pentylamine (R=H).

Both iodobiotin derivatives 2 exhibited ≧95% binding to immobilized avidin. Incubation of the products 2 with mouse serum resulted in no loss of the ability of 2 to bind to immobilized avidin. Biodistribution studies of 2 in male BALB/c mice showed rapid clearance from the blood (similar to $^{186}$Re-chelate-biotin conjugates described above). The radioiodbiotin 2 had decreased hepatobiliary excretion as compared to the $^{186}$Re-chelate-biotin conjugate; urinary excretion was increased as compared to the $^{186}$Re-chelate-biotin conjugate. Analysis of urinary metabolites of 2 indicated deiodination and cleavage of the biotin amide bond; the metabolites showed no binding to immobilized avidin. In contrast, metabolites of the $^{186}$Re-chelate-biotin conjugate appear to be excreted in urine as intact biotin conjugates. Intestinal uptake of 2 is <50% that of the $^{186}$Re-chelate-biotin conjugate. These biodistribution properties of 2 provided enhanced whole body clearance of radioisotope and indicate the advantageous use of 2 within pretargeting protocols.

$^{131}$I-PIP-biocytin was evaluated in a two-step pretargeting procedure in tumor-bearing mice. Briefly, female nude mice were injected subcutaneously with LS-180 tumor cells; after 7 d, the mice displayed 50–100 mg tumor xenografts. At t=0, the mice were injected with 200 μg of NR-LU-10-avidin conjugate labeled with $^{125}$I using PIP-NHS (see Example IV.A.). At t=36 h, the mice received 42 μg of $^{131}$I-PIP-biocytin. The data showed immediate, specific tumor localization, corresponding to ≈1.5 $^{131}$I-PIP-biocytin molecules per avidin molecule.

The described radiohalogenated biotin compounds are amenable to the same types of modifications described in Example VI above for $^{186}$Re-chelate-biotin conjugates. In particular, the following PIP-polylysine-biotin molecule is made by trace labeling polylysine with $^{125}$I-PIP, followed by extensive biotinylation of the polylysine.

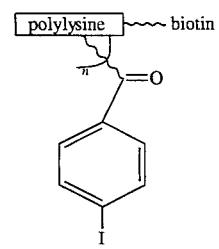

Assessment of $^{125}$I binding to immobilized avidin ensures that all radioiodinated species also contain at least an equivalent of biotin.

EXAMPLE VIII

Preparation of Biotinylated Antibody (Thiol) Through Endogenous Antibody Sulfhydryl Groups or Sulfhydryl-Generating Compounds Certain antibodies have available for reaction endogenous sulfhydryl groups. If the antibody to be biotinylated contains endogenous sulfhydryl groups, such antibody is reacted with N-iodoacetyl-n'-biotinyl hexylene diamine (as described in Example IV.A., above). The availability of one or more endogenous sulfhydryl groups obviates the need to expose the antibody to a reducing agent, such as DTT, which can have other detrimental effects on the biotinylated antibody.

Alternatively, one or more sulfhydryl groups are attached to a targeting moiety through the use of chemical compounds or linkers that contain a terminal sulfhydryl group. An exemplary compound for this purpose is iminothiolane. As with endogenous sulfhydryl groups (discussed above), the detrimental effects of reducing agents on antibody are thereby avoided.

EXAMPLE IX

Two-Step Pretargeting Methodology That Does Not Induce Internalization

A NR-LU-13-avidin conjugate is prepared as follows. Initially, avidin is derivatized with N-succinimidyl 4-(N-maleimidomethyl)cyclohexane-1-carboxylate (SMCC).

SMCC-derived avidin is then incubated with NR-LU-13 in a 1:1 molar ratio at pH 8.5 for 16 h. Unreacted NR-LU-13 and SMCC-derived avidin are removed from the mixture using preparative size exclusion HPLC. Two conjugates are obtained as products—the desired 1:1 NR-LU-13-avidin conjugate as the major product; and an incompletely characterized component as the minor product.

A $^{99m}$Tc-chelate-biotin conjugate is prepared as in Example II, above. The NR-LU-13-avidin conjugate is administered to a recipient and allowed to clear from the circulation. One of ordinary skill in the art of radioimmunoscintigraphy is readily able to determine the optimal time for NR-LU-13-avidin conjugate tumor localization and clearance from the circulation. At such time, the $^{99m}$Tc-chelate-biotin conjugate is administered to the recipient. Because the 99mTc-chelate-biotin conjugate has a molecular weight of $\approx 1,000$, crosslinking of NR-LU-13-avidin molecules on the surface of the tumor cells is dramatically reduced or eliminated. As a result, the $^{99m}$Tc diagnostic agent is retained at the tumor cell surface for an extended period of time. Accordingly, detection of the diagnostic agent by imaging techniques is optimized; further, a lower dose of radioisotope provides an image comparable to that resulting from the typical three-step pretargeting protocol.

Optionally, clearance of NR-LU-13-avidin from the circulation may be accelerated by plasmapheresis in combination with a biotin affinity column. Through use of such column, circulating NR-LU-13-avidin will be retained extracaporeally, and the recipient's immune system exposure to a large, proteinaceous immunogen (i.e., avidin) is minimized.

An alternative procedure for clearing NR-LU-13-avidin from the circulation without induction of internalization involves administration of biotinylated, high molecular weight molecules, such as liposomes, IgM and other molecules that are size excluded from ready permeability to tumor sites. When such biotinylated, high molecular weight molecules aggregate with NR-LU-13-avidin, the aggregated complexes are readily cleared from the circulation via the RES.

EXAMPLE X

Enhancement of Therapeutic Agent Internalization Through Avidin Crosslinking

The ability of multivalent avidin to crosslink two or more biotin molecules (or chelate-biotin conjugates) is advantageously used to improve delivery of therapeutic agents. More specifically, avidin crosslinking induces internalization of crosslinked complexes at the target cell surface.

Biotinylated NR-CO-04 (lysine) is prepared according to the methods described in Example IV.A., above. Doxorubicin-avidin conjugates are prepared by standard conjugation chemistry. The biotinylated NR-CO-04 is administered to a recipient and allowed to clear from the circulation. One of ordinary skill in the art of radioimmunotherapy is readily able to determine the optimal time for biotinylated NR-CO-04 tumor localization and clearance from the circulation. At such time, the doxorubicin-avidin conjugate is administered to the recipient. The avidin portion of the doxorubicin-avidin conjugate crosslinks the biotinylated NR-CO-04 on the cell surface, inducing internalization of the complex. Thus, doxorubicin is more efficiently delivered to the target cell.

In a first alternative protocol, a standard three-step pretargeting methodology is used to enhance intracellular delivery of a drug to a tumor target cell. By analogy to the description above, biotinylated NR-LU-05 is administered, followed by avidin (for blood clearance and to form the middle layer of the sandwich at the target cell-bound biotinylated antibody). Shortly thereafter, and prior to internalization of the biotinylated NR-LU-05-avidin complex, a methotrexate-biotin conjugate is administered.

In a second alternative protocol, biotinylated NR-LU-05 is further covalently linked to methotrexate. Subsequent administration of avidin induces internalization of the complex and enhances intracellular delivery of drug to the tumor target cell.

In a third alternative protocol, NR-CO-04-avidin is administered to a recipient and allowed to clear from the circulation and localize at the target site. Thereafter, a polybiotinylated species (such as biotinylated poly-L-lysine, as in Example IV.B., above) is administered. In this protocol, the drug to be delivered may be covalently attached to either the antibody-avidin component or to the polybiotinylated species. The polybiotinylated species induces internalization of the (drug)-antibody-avidin-polybiotin-(drug) complex.

EXAMPLE XI

Synthesis of DOTA-Biotin Conjugates

A. Synthesis of Nitro-Benzyl-DOTA

The synthesis of aminobenzyl-DOTA was conducted substantially in accordance with the procedure of McMurry et al., *Bioconjugate Chem.*, 3: 108–117, 1992. The critical step in the prior art synthesis is the intermolecular cyclization between disuccinimidyl N-(tert-butoxycarbonyl)iminodiacetate and N-(2-aminoethyl)-4-nitrophenyl alaninamide to prepare 1-(tert-butoxycarbonyl)-5-(4-nitrobenzyl)-3,6,11-trioxo-1,4,7,10-tetraazacyclododecane. In other words, the critical step is the intermolecular cyclization between the bis-NHS ester and the diamine to give the cyclized dodecane. McMurry et al. conducted the cyclization step on a 140 mmol scale, dissolving each of the reagents in 100 ml DMF and adding via a syringe pump over 48 hours to a reaction pot containing 4 liters dioxane.

A 5× scale-up of the McMurry et al. procedure was not practical in terms of reaction volume, addition rate and reaction time. Process chemistry studies revealed that the reaction addition rate could be substantially increased and that the solvent volume could be greatly reduced, while still obtaining a similar yield of the desired cyclization product. Consequently on a 30 mmol scale, each of the reagents was dissolved in 500 ml DMF and added via addition funnel over 27 hours to a reaction pot containing 3 liters dioxane. The addition rate of the method employed involved a 5.18 mmol/hour addition rate and a 0.047M reaction concentration.

B. Synthesis of a D-Alanine-Linked Conjugate with a Preserved Biotin Carboxy Moiety A reaction scheme to form a compound of the following formula is discussed below.

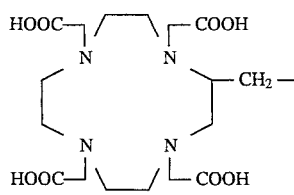 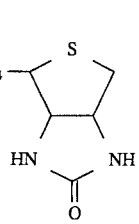

The D-alanine-linked conjugate was prepared by first coupling D-alanine (Sigma Chemical Co.) to biotin-NHS ester. The resultant biotinyl-D-alanine was then activated with 1-(3-dimethylaminopropyl)-3-ethyl-carbodiimide hydrochloride (EDCI) and N-hydroxysuccinimide (NHS). This NHS ester was reacted in situ with DOTA-aniline to give the desired product which was purified by preparative HPLC.

More specifically, a mixture of D-alanine (78 mg, 0.88 mmol, 1.2 equivalents), biotin-NHS ester (250 mg, 0.73 mmol, 1.0 equivalent), triethylamine (0.30 ml, 2.19 mmol, 3.0 equivalents) in DMF (4 ml) was heated at 110° C. for 30 minutes. The solution was cooled to 23° C. and evaporated. The product solid was acidified with glacial acetic acid and evaporated again. The product biotinyl-D-alanine, a white solid, was suspended in 40 ml of water to remove excess unreacted D-alanine, and collected by filtration. Biotinyl-D-alanine was obtained as a white solid (130 mg, 0.41 mmol) in 47% yield.

NHS (10 mg, 0.08 mmol) and EDCI (15 mg, 0.07 mmol) were added to a solution of biotinyl-D-alanine (27 mg, 0.08 mmol) in DMF (1 ml). The solution was stirred at 23° C. for 60 hours, at which time TLC analysis indicated conversion of the carboxyl group to the N-hydroxy succinimidyl ester. Pyridine (0.8 ml) was added followed by DOTA-aniline (20 mg, 0.04 mmol). The mixture was heated momentarily at approximately 100° C., then cooled to 23° C. and evaporated. The product, DOTA-aniline-D-alanyl-biotinamide was purified by preparative HPLC.

C. Synthesis of N-hydroxyethyl-Linked Conjugate

Iminodiacetic acid dimethyl ester is condensed with biotin-NHS-ester to give biotinyl dimethyl iminodiacetate. Hydrolysis with one equivalent of sodium hydroxide provides the monomethyl ester after purification from under and over hydrolysis products. Reduction of the carboxyl group with borane provides the hydroxyethyl amide. The hydroxyl group is protected with t-butyl-dimethyl-silylchloride. The methyl ester is hydrolysed, activated with EDCI and condensed with DOTA-aniline to form the final product conjugate.

D. Synthesis of N-Me-LC-DOTA-Biotin

A reaction scheme is shown below.

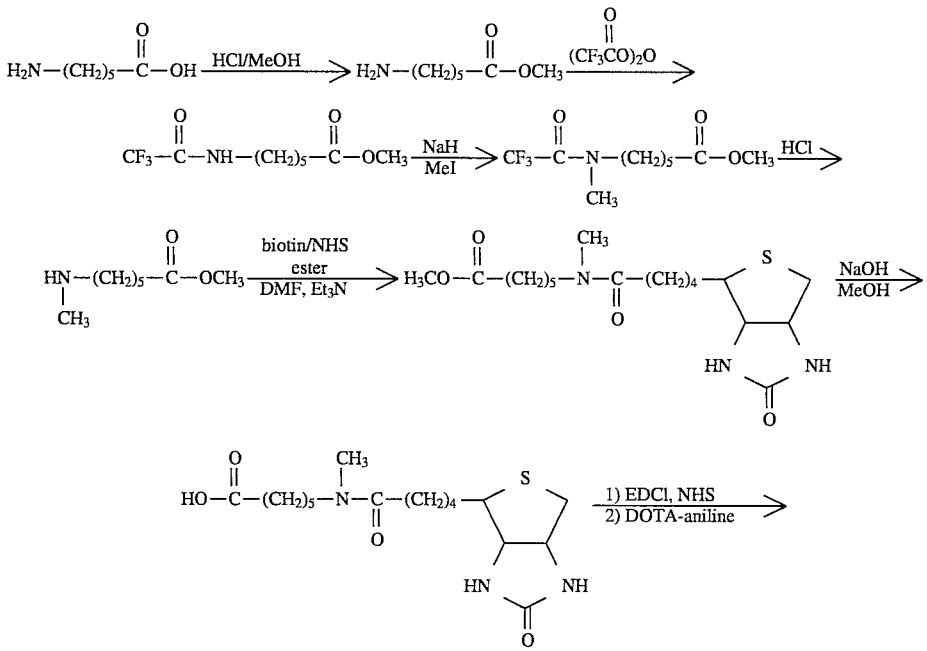

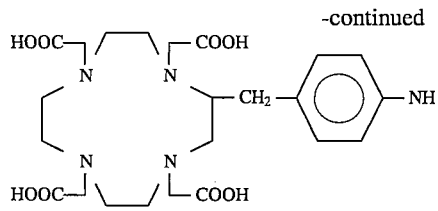 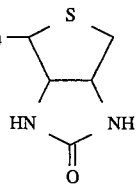

Esterification of 6-Aminocaproic acid (Sigma Chemical Co.) was carried out with methanolic HCl. Trifluoroacetylation of the amino group using trifluoroacetic anhydride gave N-6-(methylcaproyl)trifluoroacetamide. The amide nitrogen was methylated using sodium hydride and iodomethane in tetrahydrofuran. The trifluoroacetyl protecting group was cleaved in acidic methanol to give methyl 6-methylamino-caproate hydrochloride. The amine was condensed with biotin-NHS ester to give methyl N-methyl-caproylamido-biotin. Saponification afforded the corresponding acid which was activated with EDCI and NHS and, in situ, condensed with DOTA-aniline to give DOTA-benzylamido-N-methyl-caproylamido-biotin.

1. Preparation of methyl 6-aminocaproate hydrochloride

Hydrogen chloride (gas) was added to a solution of 20.0 g (152 mmol) of 6-aminocaproic acid in 250 ml of methanol via rapid bubbling for 2–3 minutes. The mixture was stirred at 15°–25° C. for 3 hours and then concentrated to afford 27.5 g of the product as a white solid (99%):

H-NMR (DMSO) 9.35 (1 H, broad t), 3.57 (3H, s), 3.14 (2H, quartet), 2.28 (2H, t), 1.48 (4H, multiplet), and 1.23 ppm (2H, multiplet).

2. Preparation of N-6-(methylcaproyl)trifluoroacetamide

To a solution of 20.0 g (110 mmol) of methyl 6-aminocaproate hydrochloride in 250 ml of dichloromethane was added 31.0 ml (22.2 mmol) of triethylamine. The mixture was cooled in an ice bath and trifluoroacetic anhydride (18.0 ml, 127 mmol) was added over a period of 15–20 minutes. The mixture was stirred at 0°–10° C. for 1 hour and concentrated. The residue was diluted with 300 ml of ethyl acetate and saturated aqueous sodium bicarbonate (3×100 ml). The organic phase was dried over anhydrous magnesium sulfate, filtered and concentrated to afford 26.5 g of the product as a pale yellow oil (100%):

H-NMR (DMSO) 3.57 (3H, s), 3.37 (2H, t), 3.08 (1.9H, quartet, N—CH$_3$), 2.93 (1.1H, s, N—CH$_3$), 2.30 (2H, t), 1.52 (4H, multiplet), and 1.23 ppm (2H, multiplet).

3. Preparation of methyl 6-N-methylamino-caproate hydrochloride

To a solution of 7.01 g (29.2 mmol) of N-6-(methylcaproyl)-trifluoroacetamide in 125 ml of anhydrous tetrahydrofuran was slowly added 1.75 g of 60% sodium hydride (43.8 mmol) in mineral oil. The mixture was stirred at 15°–25° C. for 30 minutes and then 6.2 g (43.7 mmol) of iodomethane was added. The mixture was stirred at 15°–25° C. for 17 hours and then filtered through celite. The solids were rinsed with 50 ml of tetrahydrofuran. The filtrates were combined and concentrated. The residue was diluted with 150 ml of ethyl acetate and washed first with 5% aqueous sodium sulfite (2×100 ml) and then with 100 ml of 1N aqueous hydrochloric acid. The organic phase was dried over anhydrous magnesium sulfate, filtered and concentrated to afford a yellow oily residue. The residue was diluted with 250 ml of methanol and then hydrogen chloride (gas) was rapidly bubbled into the mixture for 2–3 minutes. The resultant mixture was refluxed for 18 hours, cooled and concentrated. The residue was diluted with 150 ml of methanol and washed with hexane (3 ×150 ml) to remove mineral oil previously introduced with NaH. The methanol phase was concentrated to afford 4.91 g of the product as a yellow oil (86%):

H-NMR (DMSO) 8.80 (2H, broad s), 3.58 (3H, s), 2.81 (2H, multiplet), 2.48 (3H, s), 2.30 (2H, t), 1.52 (4H, multiplet), and 1.29 ppm (2H, multiplet).

4. Preparation of methyl 6-(N-methylcaproylamido-biotin

N-hydroxysuccinimidyl biotin (398 mg, 1.16 mmol) was added to a solution of methyl 6-(N-methyl) aminocaproate hydrochloride (250 mg, 1.28 mmol) in DMF (4.0 ml) and triethylamine (0.18 ml, 1.28 mmol). The mixture was heated in an oil bath at 100° C. for 10 minutes. The solution was evaporated, acidified with glacial acetic acid and evaporated again. The residue was chromatographed on a 25 mm flash chromatography column manufactured by Ace Glass packed with 50 g silica (EM Science, Gibbstown, N.J., particle size 0.40–0.63 mm) eluting with 15% MeOH/EtOAc. The product was obtained as a yellow oil (390 mg) in 79% yield.

5. Preparation of 6-(N-methyl-N-biotinyl) amino caproic acid

To a solution of methyl 6-(N-methyl-caproylamido-biotin (391 mg, 1.10 mmol) in methanol (2.5 ml) was added a 0.95N NaOH solution (1.5 ml). This solution was stirred at 23° C. for 3 hours. The solution was neutralized by the addition of 1.0M HCl (1.6 ml) and evaporated. The residue was dissolved in water, further acidified with 1.0M HCl (0.4 ml) and evaporated. The gummy solid residue was suspended in water and agitated with a spatula until it changed into a white powder. The powder was collected by filtration with a yield of 340 mg. 6. Preparation of DOTA-benzylamido-N-methyl-caproylamido-biotin A suspension of 6-(N-methyl-N-biotinyl)amino caproic acid (29 mg, 0.08 mmol) and N-hydroxysuccinimide (10 mg, 0.09 mmol) in DMF (0.8 ml) was heated over a heat gun for the short time necessary for the solids to dissolve. To this heated solution was added EDCI (15 mg, 0.08 mmol). The resultant solution was stirred at 23° C. for 20 hours. To this stirred solution were added aminobenzyl-DOTA (20 mg, 0.04 mmol) and pyridine (0.8 ml). The mixture was heated over a heat gun for 1 minute. The product was isolated by preparative HPLC, yielding 3 mg.

E. Synthesis of a bis-DOTA Conjugate with a Preserved Biotin Carboxy Group

A reaction scheme is shown below.

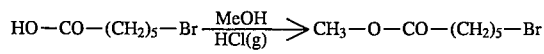

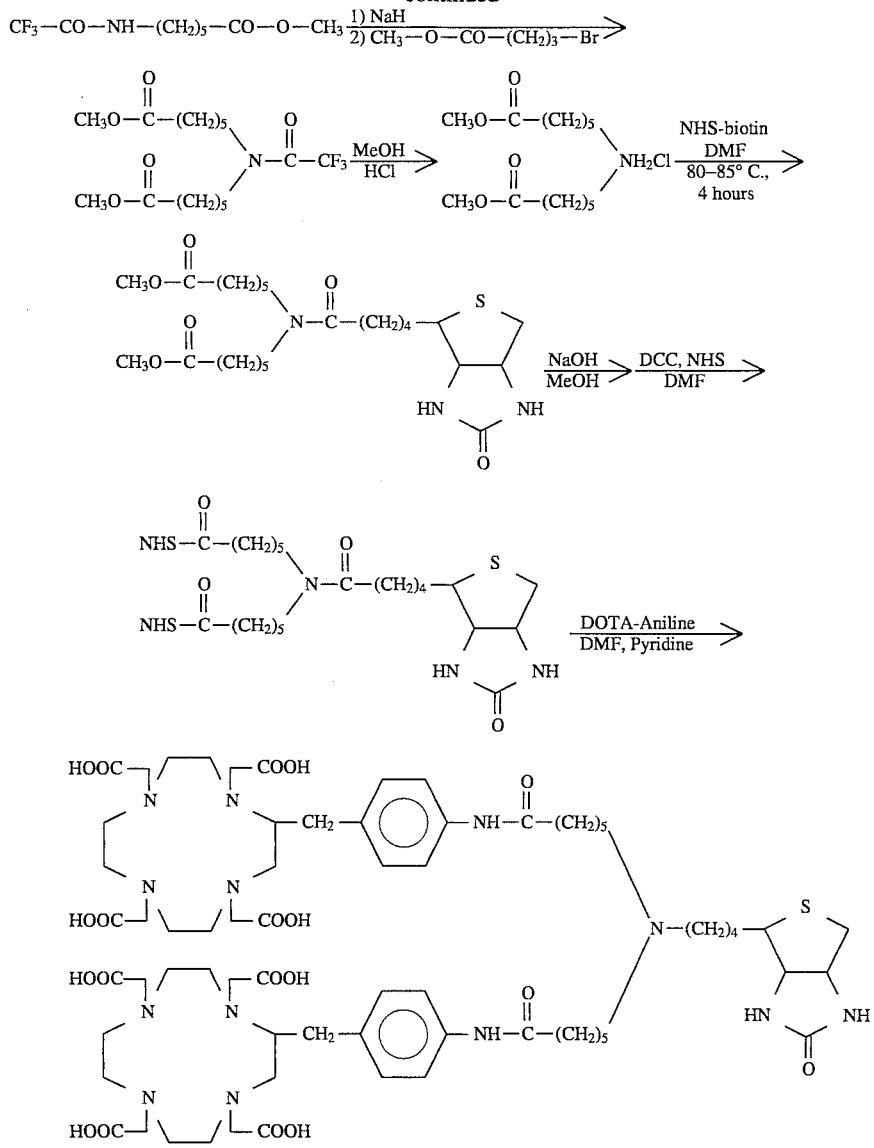

1. Preparation of methyl 6-bromocaproate (methyl 6-bromohexanoate)

Hydrogen chloride (gas) was added to a solution of 5.01 g (25.7 mmol) of 6-bromocaproic acid in 250 ml of methanol via vigorous bubbling for 2–3 minutes. The mixture was stirred at 15°–25° C. for 3 hours and then concentrated to afford 4.84 g of the product as a yellow oil (90%):

H-NMR (DMSO) 3.58 (3H, s), 3.51 (2H, t), 2.29 (2H, t), 1.78 (2H, pentet), and 1.62–1.27 ppm (4H, m).

2. Preparation of N, N-bis- (methyl 6-hexanoyl ) amine hydrochloride. To a solution of 4.01 g (16.7 mmol) of N-(methyl 6-hexanoyl)-trifluoroacetamide (prepared in accordance with section D.2. herein) in 125 ml of anhydrous tetrahydrofuran was added 1.0 g (25 mmol) of 60% sodium hydride in mineral oil. The mixture was stirred at 15°–25° C. for 1 hour and then 3.50 g (16.7 mmol) of methyl 6-bromocaproate was added and the mixture heated to reflux. The mixture was stirred at reflux for 22 hours. NMR assay of an aliquot indicated the reaction to be incomplete. Consequently, an additional 1.00 g (4.8 mmol) of methyl 6-bromocaproate was added and the mixture stirred at reflux for 26 hours. NMR assay of an aliquot indicated the reaction to be incomplete. An additional 1.0 g of methyl 6-bromocaproate was added and the mixture stirred at reflux for 24 hours. NMR assay of an aliquot indicated the reaction to be near complete. The mixture was cooled and then directly filtered through celite. The solids were rinsed with 100 ml of tetrahydrofuran. The filtrates were combined and concentrated. The residue was diluted with 100 ml of methanol and washed with hexane (3×100 ml) to remove the mineral oil introduced with the sodium hydride. The methanol phase was treated with 6 ml of 10N aqueous sodium hydroxide and stirred at 15°–25° C. for 3 hours. The mixture was concentrated. The residue was diluted with 100 ml of deionized water and acidified to pH 2 with concentrated HCl. The mixture was washed with ether (3×100 ml). The aqueous phase was concentrated, diluted with 200 ml of dry methanol and then hydrogen chloride gas was bubbled through the mixture for 2–3 minutes. The mixture was stirred at 15°–25° C. for 3 hours and then concentrated. The residue was diluted with 50 ml of dry methanol and filtered to remove inorganic salts. The filtrate was concentrated to afford 1.98 g of the product as a white solid (38%):

H-NMR (DMSO) 8.62 (2H, m) 3.58 (6H, s), 2.82 (4H, m) 2.30 (4H, t), 1.67–1.45 (8H, m) and 1.38–1.22 ppm (4H, m).

3. Preparation of N,N'-bis-(methyl 6-hexanol)biotinamide

To a solution of 500 mg (1.46 mmol) of N-hydroxysuccinimidyl biotin in 15 ml of dry dimethylformamide was added 600 mg (1.94 mmol) of N,N-bis-(methyl 6-hexanoyl)amine hydrochloride followed by 1.0 ml of triethylamine. The mixture was stirred at 80°–85° C. for 3 hours and then cooled and concentrated. The residue was chromatographed on silica gel, eluting with 20% methanol/ethyl acetate, to afford 620 mg of the product as a near colorless oil (85%):

H-NMR (CDCl$_3$) 5.71 (1H, s), 5.22 (1H, s), 4.52 (1H, m), 4.33 (1H, m), 3.60 (3H, s), 3.58 (3H, s), 3.34–3.13 (5H, m), 2.92 (1H, dd), 2.75 (1H, d), 2.33 ( 6H, m) and 1.82–1.22 ppm ( 18H, m); TLC-R$_f$ 0.39 (20: 80 methanol/ethyl acetate).

4. Preparation of N,N-bis-(6-hexanoyl)biotinamide

To a solution of 610 mg (0.819 mmol) of N,N-bis-(methyl 6-hexanoyl)-biotinamide in 35 ml of methanol was added 5.0 ml of 1N aqueous sodium hydroxide. The mixture was stirred at 15°–25° C. for 4.5 hours and then concentrated. The residue was diluted with 50 ml of deionized water acidified to pH 2 with 1N aqueous hydrochloric acid at 4° C. The product, which precipitated out as a white solid, was isolated by vacuum filtration and dried under vacuum to afford 482 mg (84%):

H-NMR (DMSO) 6.42 (1H, s), 6.33 (1H, s), 4.9 (1H, m), 4.12 (1H, m), 3.29–3.04 (5H, m), 2.82 (1H, dd), 2.57 (1H, d), 2.21 (6H, m) and 1.70–1.10 ppm (18H, m).

5. Preparation of N',N'-bis-(N-hydroxysuccinimidyl 6-hexanoyl)-biotinamide

To a solution of 220 mg (0.467 mmol) of N,N-bis-(6-hexanoyl)-biotinamide in 3 ml of dry dimethylformamide was added 160 mg (1.39 mmol) of N-hydroxysuccinimide followed by 210 mg (1.02 mmol) of dicyclohexyl-carbodiimide. The mixture was stirred at 15°–25° C. for 17 hours and then concentrated. The residue was chromatographed on silica gel, eluting with 0.1: 20: 80 acetic acid/methanol/ethyl acetate, to afford 148 mg of the product as a foamy off-white solid (48%):

H-NMR (DMSO) 6.39 (1H, s), 6.32 (1H, s), 4.29 (1H, m), 4.12 (1H, m), 3.30–3.03 (5H, m), 2.81 (9H, dd and s), 2.67 (4H, m), 2.57 (1H, d), 2.25 (2H, t), 1.75–1.20 (18H, m); TLC-R$_f$ 0.37 (0.1:20:80 acetic acid/methanol/ethyl acetate).

6. Preparation of N,N-bis-(6-hexanoylamidobenzyl-DOTA)-biotinamide

To a mixture of 15 mg of DOTA-benzylamine and 6 0 mg of N',N'-bis-(N-hydroxysuccinimidyl 6-hexanoyl)-biotinamide in 1.0 ml of dry dimethylformamide was added 0.5 ml of dry pyridine. The mixture was stirred at 45°–50° C. for 4.5 hours and at 15°–25° C. for 12 hours. The mixture was concentrated and the residue chromatographed on a 2.1×2.5 cm octadecylsilyl (ODS) reverse-phase preparative HPLC column eluting with a—20 minute gradient profile of 0.1:95:5 to 0.1:40:60 trifluoroacetic acid:water:acetonitrile at 13 ml/minute to afford the desired product. The retention time was 15.97 minutes using the aforementioned gradient at a flow rate of 1.0 ml/minute on a 4.6 mm×25 cm ODS analytical HPLC column.

F. Synthesis of an N-methyl-glycine Linked Conjugate

A reaction scheme for this synthesis is shown below.

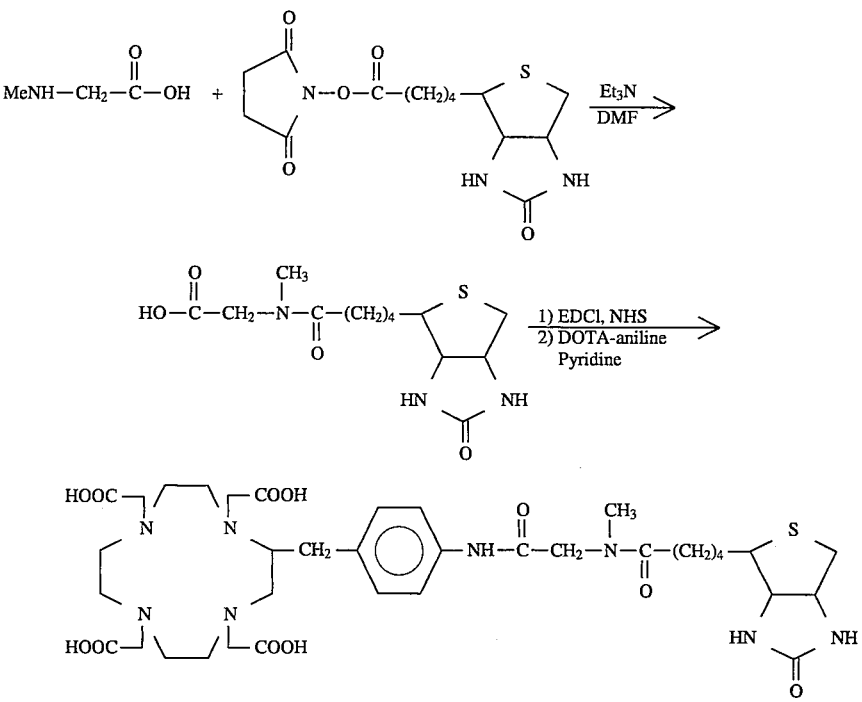

The N-methyl glycine-linked DOTA-biotin conjugate was prepared by an analogous method to that used to prepare D-alanine-linked DOTA-biotin conjugates. N-methyl-glycine (trivial name sarcosine, available from Sigma Chemical Co.) was condensed with biotin-NHS ester in DMF and triethylamine to obtain N-methyl glycyl-biotin. N-methylglycyl biotin was then activated with EDCI and NHS. The resultant NHS ester was not isolated and was condensed in situ with DOTA-aniline and excess pyridine. The reaction solution was heated at 60° C. for 10 minutes and then evaporated. The residue was purified by preparative HPLC to give [(N-methyl-N-biotinyl)-N-glycyl]-aminobenzyl-DOTA.

1. Preparation of (N-methyl)glycyl biotin

DMF (8.0 ml) and triethylamine (0.61 ml, 4.35 mmol) were added to solids N-methyl glycine (182 mg, 2.05 mmol)

and N-hydroxy-succinimidyl biotin (500 mg, 1.46 mmol). The mixture was heated for 1 hour in an oil bath at 85° C. during which time the solids dissolved producing a clear and colorless solution. The solvents were then evaporated. The yellow oil residue was acidified with glacial acetic acid, evaporated and chromatographed on a 27 mm column packed with 50 g silica, eluting with 30% MeOH/EtOAc 1% HOAc to give the product as a white solid (383 mg) in 66% yield.

H-NMR (DMSO): 1.18–1.25 (m, 6H, (CH$_2$)$_3$), 2.15, 2.35 (2 t's, 2H, CH$_2$CO), 2.75 (m, 2H, SCH$_2$), 2.80, 3.00 (2 s's, 3H, NCH$_3$), 3.05–3.15 (m, 1H, SCH), 3.95, 4.05 (2 s's, 2H, CH$_2$N), 4.15, 4.32 (2 m's, 2H, 2CHN's), 6.35 (s, NH), 6.45 (s, NH).

2. Preparation of [(N-methyl-N-biotinyl)glycyl]aminobenzyl-DOTA

N-hydroxysuccinimide (10 mg, 0.08 mmol) and EDCI (15 mg, 6.08 mmol) were added to a solution of (N-methylglycyl biotin (24 mg, 0.08 mmol) in DMF (1.0 ml). The solution was stirred at 23 ° C. for 64 hours. Pyridine (0.8 ml) and aminobenzyl-DOTA (20 mg, 0.04 mmol) were added. The mixture was heated in an oil bath at 63° C. for 10 minutes, then stirred at 23° C. for 4 hours. The solution was evaporated. The residue was purified by preparative HPLC to give the product as an off white solid (8 mg, 0.01 mmol) in 27% yield.

H-NMR (D$_2$O): 1.30–1.80 (m, 6H), 2.40, 2.55 (2 t's, 2H, CH$_2$CO), 2.70–4.2 (complex multiplet), 4.35 (m, CHN), 4.55 (m, CHN), 7.30 (m, 2H, benzene hydrogens), 7.40 (m, 2H, benzene hydrogens).

G. Synthesis of a Short Chain Amine-Linked Conjugate with a Reduced Biotin Carboxy Group A two-part reaction scheme is shown below.

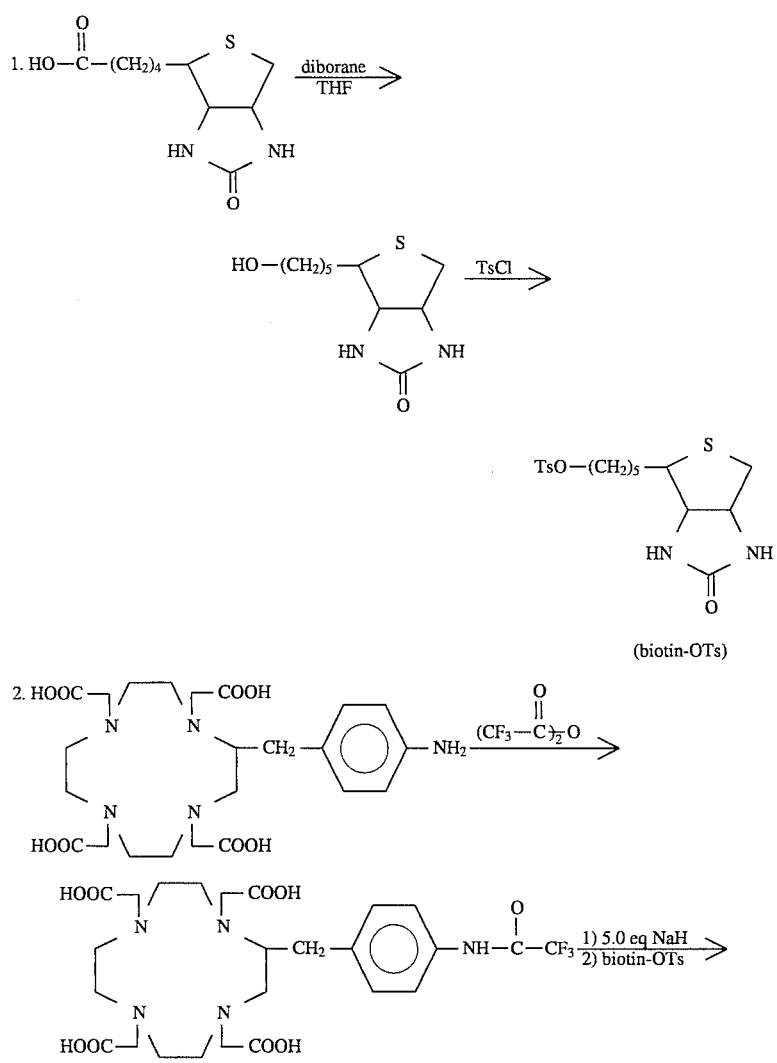

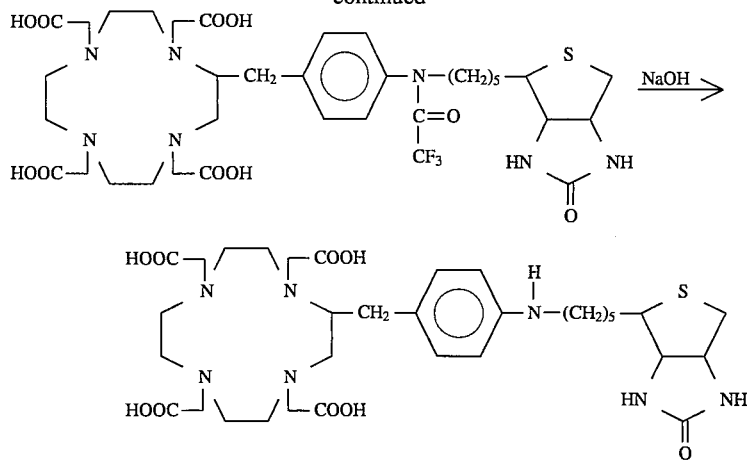

The biotin carboxyl group is reduced with diborane in THF to give a primary alcohol. Tosylation of the alcohol with tosyl chloride in pyridine affords the primary tosylate. Aminobenzyl DOTA is acylated with trifluoroacetic anhydride in pyridine to give (N-trifluoroacetyl)aminobenzyl-DOTA. Deprotonation with 5.0 equivalents of sodium hydride followed by displacement of the biotin tosylate provides the (N-trifluoracetamido-N-descarboxylbiotinyl)aminobenzyl-DOTA. Acidic cleavage of the N-trifluoroacetamide group with HCl(g) in methanol provides the amine-linked DOTA-biotin conjugate.

EXAMPLE XII

Human Clinical Trial: Three-Step Pretargeting

Patients were selected on the basis of a variety of criteria. The three-step pretargeting protocol to which such patients were subjected proceeded as follows:

Step 1—Patients received 10 mg whole NR-LU-10-LC-biotin conjugate prepared in accordance with the procedure described in Example IV. In some cases, the conjugate was radiolabeled with Tc-99m in accordance with the procedure referenced above for radiolabeling NR-LU-10 Fab to facilitate monitoring of the conjugate in vivo. The NR-LU-10-LC-biotin conjugate, either radiolabeled or non-radiolabeled, was diluted in 30 ML of normal saline and administered by intravenous injection over 3–5 minutes. The conjugate was administered within 4 hours after completion of the radiolabeling procedure and exhibited 20–25 mCi activity when administered.

Step 2—Avidin was administered intravenously 24–36 hours after administration of the NR-LU-10-LC-biotin conjugate. The avidin administration was conducted in two stages: 3–5 mg in 5 mL of physiological solution as a rapid bolus dose and 40–80 mg in 100 mL of physiological solution 30 minutes later. Some patients received radiolabeled avidin (10–15 mCi activity at the time of administration) to facilitate in vivo monitoring of this component of the three-step pretargeting system. Avidin was also radiolabeled substantially in accordance with the procedure referenced above for NR-LU-10 Fab radiolabeling.

Step 3—Diethylenetriaminepentacetic acid-alpha, W-bis-(biocytinamide) (DTPA-bis-biotin, available from Sigma Chemical Company, St. Louis, Mo.) was radiolabeled with In-111 as set forth below. DTPA-biotin was diluted in PBS, pH 7.4, to a concentration of 2 micrograms/microliter. The solution was sterilized by 0.22 mm millipore filtration. $^{111}$InCl$_3$ was diluted in citrate buffer (0.02M; pH 6.5) to 740 kBq/µl. The two reagents were mixed and allowed to react at room temperature for 10 minutes. Generally, a 98% chelation of In-111 to DTPA-biotin was achieved, as verified by paper chromatography. Administration of 2–5 mg of In-111-DTPA-biotin (5–10 mCi activity) diluted in 5 mL of saline was conducted intravenously, over 1 minute, 24 hours after avidin administration. The patients were evaluated for 24 hours following administration of In-111-DTPA-biotin.

A 66 year old male presented with a large primary lesion in the ascending colon and a small lesion in the transverse colon (polyp). This patient was subjected to a three-step pretargeting protocol as follows:

t=0; 10 mg monoclonal antibody-biotin t=25 hour; 10 mg avidin;

t=25.3 hour; 90 mg avidin; and t=24 hour; 6 mCi In-111-DTPA-biotin.

Images were taken and analyzed by the attending physician. The large lesion was visualized in a 2 hour SPECT image.

EXAMPLE XIII

Three-Step Pretargeting Using Y-90

A patient presents with ovarian cancer. A monoclonal antibody (MAb) directed to an ovarian cancer cell antigen, e.g., NR-LU-10, is conjugated to biotin to form a MAb-biotin conjugate. The MAb-biotin conjugate is administered to the patient in an amount sufficient to substantially saturate the available antigenic sites at the target (which amount is at least sufficient to allow the capture of a therapeutically effective radiation dose at the target and which amount may be in excess of the maximum tolerated dose of conjugate administrable in a targeted, chelate-labeled molecule protocol, such as administration of monoclonal antibody-chelate-radionuclide conjugate). The MAb-biotin so administered is permitted to localize to target cancer cells for 24–48 hours. Next, an amount of avidin sufficient to clear non-targeted MAb-biotin conjugate and to bind to the targeted biotin is administered.

A biotin-radionuclide chelate conjugate of the type discussed in Example XI(F) above is radiolabeled with Y-90 as set forth below. Carrier free $^{90}$YCl$_3$ (available from NEN-DuPont, Wilmington, Del.) at 20–200 µl in 0.05N HCl was diluted with ammonium acetate buffer (0.5M, pH 5) to a total volume of 0.4 ml. 50 µl (500 mg/ml) of ascorbic acid and 50–100 µl (10 mg/ml) of DOTA-biotin were added to the buffered $^{90}YCl_3$ solution. The mixture was incubated for one hour at 80° C. Upon completion of the incubations, 55 µl of 100 mM DTPA was added to the mixture to chelate any unbound $^{90}Y$. The final preparation was diluted to 10 ml with 0.9% NaCl.

The radiolabeled DOTA-biotin conjugate is administered to the patient in a therapeutically effective dose. The biotin-radionuclide chelate conjugate localizes to the targeted MAb-biotin-avidin moiety or is substantially removed from the patient via the renal pathway.

Kits containing one or more of the components described above are also contemplated. For instance, radiohalogenated biotin may be provided in a sterile container for use in pretargeting procedures. A chelate-biotin conjugate provided in a sterile container is suitable for radiometallation by the consumer; such kits would be particularly amenable for use in pretargeting protocols. Alternatively, radiohalogenated biotin and a chelate-biotin conjugate may be vialed in a non-sterile condition for use as a research reagent.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An improved method of enhancing active agent localization at a target site in a mammalian recipient, which method comprises:

administering to the recipient a first conjugate comprising an antibody or antigen-binding antibody fragment and a biotin, whereupon the first conjugate localizes to the target site;

administering to the recipient avidin or streptavidin; and thereupon administering to the recipient a second conjugate comprising biotin, a linker resistant to biotinidase cleavage and an active agent, wherein second agent localization at the target site is enhanced as a result of prior localization of the first conjugate and wherein the improvement is that the second conjugate comprises a biotinidase-resistant biotin-DOTA compound of the following formula:

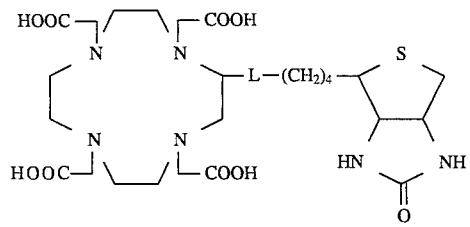

wherein a linker L is selected from the group consisting of:

1) a D-amino acid-containing linker of the formula

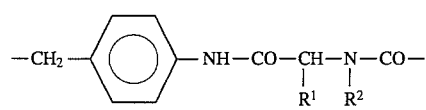

2) a linker of the formula

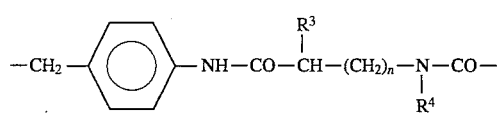

3) a linker of the formula

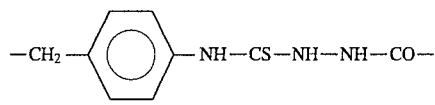

4) a linker of the formula

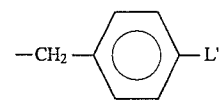

wherein L' is selected from the group consisting of:

a) $-NH-CO-(CH_2)_n-O$;

b) $-NH-$;

c) $-NH-CO-CH_2-N(R')-R''-$;

d) $-NH-CS-NH-$; and e) $-NH-CO-(CH_2)_n-NH-$, wherein $R^1$ is hydrogen, lower alkyl; lower alkyl substituted with one or more hydrophilic groups selected from the group consisting of $(CH_2)_m-OH$, $(CH_2)_m-OSO_3$, $(CH_2)_m-SO_3$,

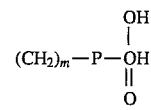

where m is 1 or 2;

glucuronide-substituted amino acids; and other glucuronide derivatives;

$R^2$ is hydrogen; lower alkyl; substituted lower alkyl having one or more substituents selected from the group consisting of hydroxy, sulfate, and phosphonate; or a hydrophilic moiety;

$R^3$ is hydrogen; an amine; a lower alkyl; a hydroxy-, sulfate- or phosphonate-substituted lower alkyl; a glucuronide; or a glucuronide-derivatized amino acid;

$R^4$ is hydrogen, lower alkyl or

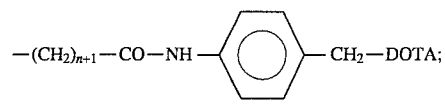

R' is hydrogen; $-(CH_2)_2-OH$ or a sulfate or phosphonate derivative thereof; or

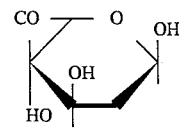

R'' is a bond or $-(CH_2)_n-CO-NH-$; and n ranges from 0–5, wherein $R^3$ and $R^4$ cannot both be hydrogen and wherein the active agent is a radionuclide.

2. A method of claim 1 wherein the targeting moiety is a monoclonal antibody, or a monovalent fragment thereof.

3. A method of claim 2 wherein the monoclonal antibody is a human, a humanized or a chimeric monoclonal antibody.

4. A method of claim 2 wherein the monoclonal antibody or fragment thereof is reactive with an antigen recognized by the antibody NR-LU-10.

5. A method of claim 1 wherein the active agent is a radionuclide selected from the group consisting of Re-186, Re-188, Tc-99m, Y-90, At-211, Pb-212, Bi-212, Sm-153, Eu-169, Lu-177, Cu-67, Rh-105, In-111, Au-198, I-123 and I-131.

6. A method of claim 1 wherein the step of administering the second conjugate is conducted by intralesional or intraarterial injection.

7. A method of claim 6 wherein the second conjugate is administered via an artery supplying target site tissue.

8. A method of claim 6 wherein the second conjugate is administered via an artery selected from the group consisting of hepatic artery, carotid artery, bronchial artery and renal artery.

9. A method of claim 1 wherein the second conjugate is administered intravenously.

10. A method of claim 1 wherein L is a D-amino acid-incorporating linker of the formula $$-CH_2-\underset{}{\bigcirc}-NH-CO-\underset{R^1}{CH}-\underset{R^2}{N}-CO-.$$

11. A method of claim 10 wherein $R^1$ is $CH_3$ and $R^2$ is H.

12. A method of claim 1 wherein L is a linker of the formula $$-CH_2-\underset{}{\bigcirc}-NH-CO-\underset{}{CH}-(CH_2)_n-\underset{R^4}{N}-CO-.$$
with $R^3$ on the CH 13. A method of claim 12 wherein $R^3$ is hydrogen; $R^4$ is $CH_3$; and n is 4.

14. A method of claim 12 wherein $R^3$ is hydrogen; $R^4$ is $CH_3$; and n is 0.

15. A method of claim 12 wherein $R^3$ is hydrogen; $R^4$ is $$-(CH_2)_5-CO-NH-\underset{}{\bigcirc}-CH_2-DOTA;$$

and n is 4.

16. A method of claim 1 wherein L is a linker of the formula $$-CH_2-\underset{}{\bigcirc}-L'-,$$

wherein L' is selected from the group consisting of:

a) $-NH-CO-(CH_2)_n-O-$;

b) $-NH-$;

c) $-NH-CO-CH_2-\underset{R'}{N}-R''-$;

d) $-NH-CS-NH-$; and e) $-NH-CO-(CH_2)_n-NH-$ or a bis-DOTA derivative thereof.

17. An improved method of enhancing active agent localization at a target site in a mammalian recipient, which method comprises:

administering to the recipient a first conjugate comprising an antibody or an antigen-binding antibody fragment thereof and a biotin, whereupon the first conjugate localizes to the target site;

administering to the recipient avidin or streptavidin; and thereupon administering to the recipient a second conjugate comprising biotin, a linker resistant to biotinidase cleavage and an active agent, wherein second agent localization at the target site is enhanced as a result of prior localization of the first conjugate and wherein the improvement is that the second conjugate comprises a biotinidase-resistant biotin-DOTA compound of the following formula:

[chemical structure showing DOTA macrocycle with four COOH groups linked via L-(CH_2)_4 to a biotin moiety]

and further wherein the linker L has the formula:

$$-CH_2-\underset{}{\bigcirc}-NH-CO-\underset{}{CH}-(CH_2)_n-\underset{R^4}{N}-CO-$$
with $R^3$ on the CH wherein $R^3$ is hydrogen, $R^4$ is $CH_3$ and n is 4; $R^3$ is hydrogen, $R^4$ is $CH_3$ and n is 0; or $R^3$ is hydrogen, $R^4$ is $$-(CH_2)_5-O-NH-\underset{}{\bigcirc}-CH_2-DOTA;$$

and n is 4; or $R^3$ is hydrogen; $R^4$ is $$-(CH_2)-CO-NH-\underset{}{\bigcirc}-CH_2-DOTA$$

and n is 0, and wherein the active agent is a radionuclide.

18. An improved method of enhancing active agent localization at a target site in a mammalian recipient, which method comprises;

administering to the recipient a first conjugate comprising an antibody or antigen-binding antibody fragment thereof and a biotin, whereupon the first conjugate localizes to the target site;

administering to the recipient avidin or streptavidin; and thereupon administering to the recipient a second conjugate comprising biotin, a linker resistant to biotinidase cleavage and an active agent, wherein second agent localization at the target site is enhanced as a result of prior localization of the first conjugate and wherein the improvement is that the second conjugate comprises a biotinidase-resistant biotin-DOTA compound of the following formula:
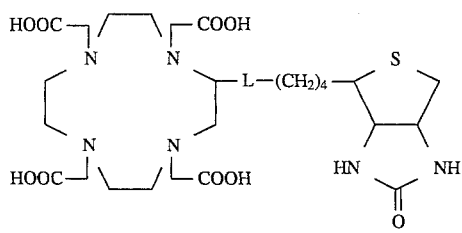
and further wherein the linker L is a D-amino acid incorporating a linker of the formula
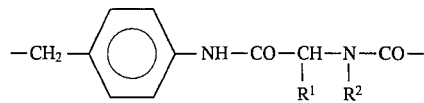
wherein $R^1$ is $CH_3$ and $R^2$ is H, and wherein the active agent is a radionuclide.
* * * * *